(12) United States Patent
Moffitt et al.

(10) Patent No.: US 8,676,308 B2
(45) Date of Patent: Mar. 18, 2014

(54) SYSTEM AND METHOD FOR MAPPING ARBITRARY ELECTRIC FIELDS TO PRE-EXISTING LEAD ELECTRODES

(71) Applicant: Boston Scientific Neuromodulation Corporation, Valencia, CA (US)

(72) Inventors: Michael A. Moffitt, Valencia, CA (US); Sridhar Kothandaraman, Valencia, CA (US); Prakash Rao, Chicago, IL (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/727,470

(22) Filed: Dec. 26, 2012

(65) Prior Publication Data
US 2013/0116751 A1    May 9, 2013

Related U.S. Application Data

(63) Continuation-in-part of application No. 12/938,282, filed on Nov. 2, 2010, now Pat. No. 8,412,345.

(60) Provisional application No. 61/257,753, filed on Nov. 3, 2009.

(51) Int. Cl.
  *A61N 1/34* (2006.01)
(52) U.S. Cl.
  USPC .................................................. 607/2; 607/59
(58) Field of Classification Search
  USPC ........................................................... 607/2, 59
  See application file for complete search history.

*Primary Examiner* — Michael Kahelin
(74) *Attorney, Agent, or Firm* — Vista IP Law Group LLP

(57) ABSTRACT

A system for a neurostimulator coupled to electrodes, and a method of providing therapy to a patient using the electrodes implanted within the patient. A target multipole relative to the electrodes is defined. The target multipole is emulated by defining an initial electrical current distribution for the electrodes, such that a first set of active electrodes respectively has electrical current values of a first polarity. Each of the electrical current values of the first polarity is compared to a first threshold value, and at least one of the electrodes in the first active electrode set is zeroed-out based on the comparison. The electrical current value of each of the zeroed-out electrode(s) is redistributed to remaining ones of the electrodes to define a new electrical current distribution for the electrodes. Electrical current is conveyed to the electrodes in accordance with the new electrical current distribution, thereby providing the therapy.

20 Claims, 14 Drawing Sheets

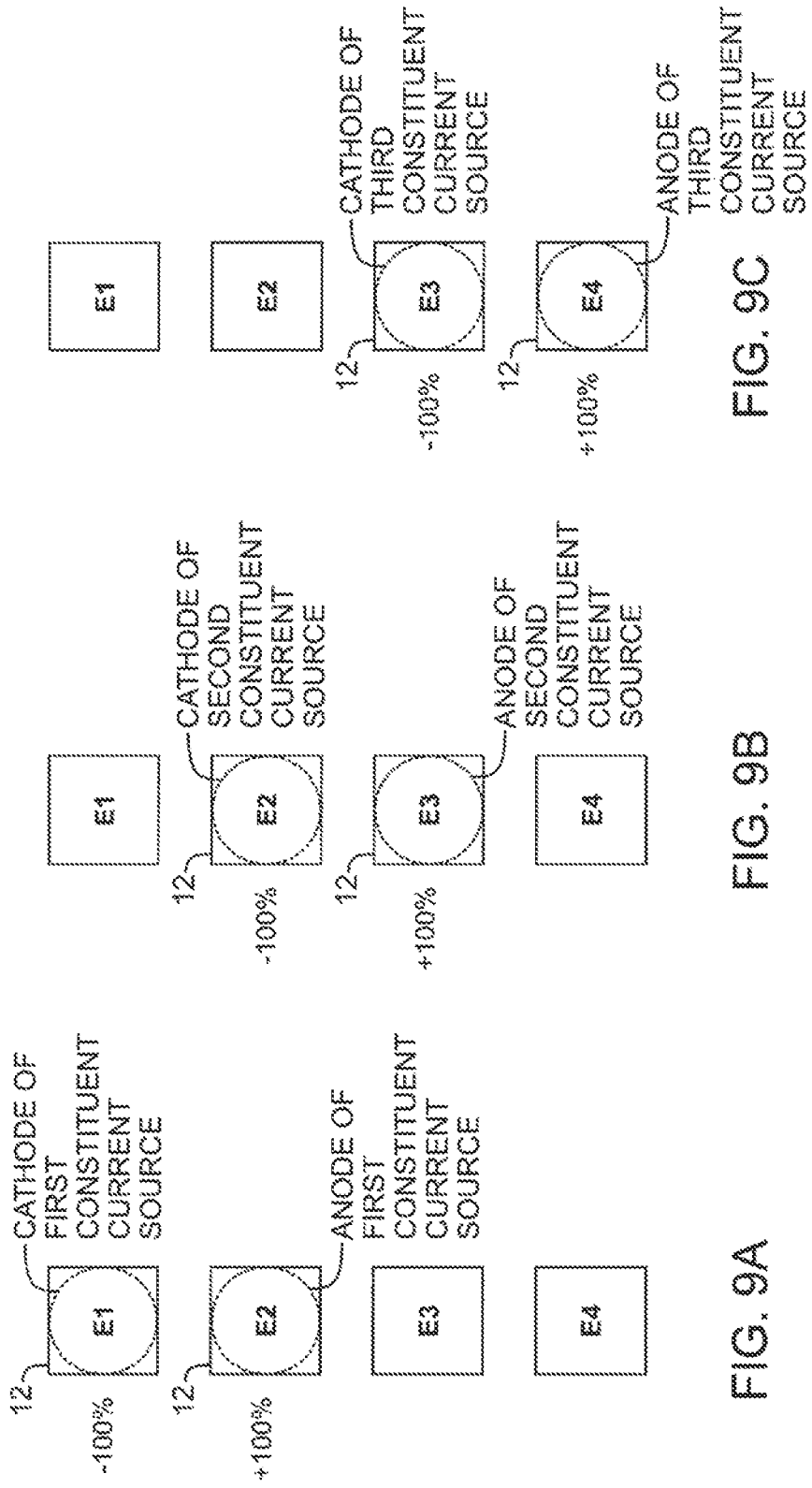

|       | $C_1$ | $C_2$ | $C_3$ |
|-------|-------|-------|-------|
| E1    | −1    | 0     | 0     |
| E2    | +1    | −1    | 0     |
| E3    | 0     | +1    | −1    |
| E4    | 0     | 0     | +1    |

FIG. 11

$$\text{Transfer Matrix A } (m \times n) \begin{bmatrix} m \text{ field potential values due to constituent source \#1} \\ m \text{ field potential values due to constituent source \#2} \\ m \text{ field potential values due to constituent source \#3} \\ \vdots \\ m \text{ field potential values due to constituent source \#n} \end{bmatrix}$$

SYSTEM AND METHOD FOR MAPPING ARBITRARY ELECTRIC FIELDS TO PRE-EXISTING LEAD ELECTRODES

RELATED APPLICATIONS

The present application is a continuation-in-part of U.S. patent application Ser. No. 12/938,282, (now U.S. Pat. No. 8,412,345) filed Nov. 2, 2010, which claims priority under 35 U.S.C. §119(e) to U.S. Provisional Patent Application No. 61/257,753, filed Nov. 3, 2009, which are hereby incorporated by reference in their entirety.

FIELD OF THE INVENTION

The present invention relates to tissue stimulation systems, and more particularly, to a system and method for programming an implantable tissue stimulator.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the stimulation lead(s) or indirectly to the stimulation lead(s) via a lead extension. The neurostimulation system may further comprise an external control device to remotely instruct the neurostimulator to generate electrical stimulation pulses in accordance with selected stimulation parameters.

Electrical stimulation energy may be delivered from the neurostimulator to the electrodes in the form of an electrical pulsed waveform. Thus, stimulation energy may be controllably delivered to the electrodes to stimulate neural tissue. The combination of electrodes used to deliver electrical pulses to the targeted tissue constituents an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, width, and rate of the electrical pulses provided through the electrode array. Each electrode combination, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode configurations).

As briefly discussed above, an external control device can be used to instruct the neurostimulator to generate electrical stimulation pulses in accordance with the selected stimulation parameters. Typically, the stimulation parameters programmed into the neurostimulator can be adjusted by manipulating controls on the external control device to modify the electrical stimulation provided by the neurostimulator system to the patient. However, the number of electrodes available, combined with the ability to generate a variety of complex stimulation pulses, presents a huge selection of stimulation parameter sets to the clinician or patient.

To facilitate such selection, the clinician generally programs the external control device, and if applicable the neurostimulator, through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback and to subsequently program the external control device with the optimum stimulation parameters. The computerized programming system may be operated by a clinician attending the patient in several scenarios.

For example, in order to achieve an effective result from SCS, the lead or leads must be placed in a location, such that the electrical stimulation will cause paresthesia, which can be characterized as an alternative sensation that replaces the pain signals sensed by the patient. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When electrical leads are implanted within the patient, the computerized programming system may be used to instruct the neurostimulator to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the neurostimulator, with a set of stimulation parameters that best addresses the painful site. Thus, the navigation session may be used to pinpoint the stimulation region or areas correlating to the pain. Such programming ability is particularly advantageous after implantation should the leads gradually or unexpectedly move, or in the case of a single-source system if the relative impedances of the contacts should change in a clinically significant way, thereby relocating the paresthesia away from the pain site. By reprogramming the external control device, the stimulation region can often be moved back to the effective pain site without having to reoperate on the patient in order to reposition the lead and its electrode array.

One known computerized programming system for SCS is called the Bionic Navigator®, available from Boston Scientific Neuromodulation Corporation, located in Valencia, Calif. The Bionic Navigator® is a software package that operates on a suitable PC and allows clinicians to program stimulation parameters into an external control device and a neurostimulator, and in particular, an external handheld programmer (referred to as a remote control) and an implantable pulse generator (IPG), respectively. Each set of stimulation parameters, including fractionalized current distribution to the electrodes (as percentage cathodic current, percentage anodic current, or off), programmed by the Bionic Navigator® may be stored in both the Bionic Navigator® and the remote control and combined into a stimulation program that can then be used to stimulate multiple regions within the patient.

Prior to creating the stimulation programs, the Bionic Navigator® may be operated by a clinician in a "manual mode" to manually select the percentage cathodic current and percentage anodic current flowing through the electrodes, or may be operated by the clinician in a "navigation mode" to electrically "steer" the current along the implanted leads in real-time, thereby allowing the clinician to determine the most efficient stimulation parameter sets that can then be stored and eventually combined into stimulation programs. In the navigation mode, the Bionic Navigator® can store selected fractionalized electrode configurations that can be displayed to the clinician as marks representing corresponding stimulation regions relative to the electrode array.

The Bionic Navigator® performs current steering in accordance with a steering or navigation table. For example, as shown in Appendix A, an exemplary navigation table, which includes a series of reference electrode combinations (for a lead of 8 electrodes) with associated fractionalized current values (i.e., fractionalized electrode configurations), can be used to gradually steer electrical current from one basic electrode combination to the next, thereby electronically steering the stimulation region along the leads.

For example, the navigation table can be used to gradually steer current between a basic electrode combination consisting of a cathodic electrode 3 and an anodic electrode 5 (represented by stimulation set 161) and either a basic electrode combination consisting of a cathodic electrode 3 and an anodic electrode 1 (represented by stimulation set 141) or a basic electrode combination consisting of a cathodic electrode 3 and an anodic electrode 6 (represented by stimulation set 181). That is, electrical current can be incrementally shifted from anodic electrode 5 to the anodic electrode 1 as one steps upward through the navigation table from stimulation set 161 to stimulation set 141, and from anodic electrode 5 to anodic electrode 6 as one steps downward through the navigation table from stimulation set 161 to stimulation set 181. The step size of the current should be small enough so that steering of the current does not result in discomfort to the patient, but should be large enough to allow refinement of a basic electrode combination in a reasonable amount of time.

While the use of navigation tables have proven to be useful in steering electrical current between electrodes in an efficient manner, that are certain inherent disadvantages associated with navigation tables. For example, assuming a current step size of 5% in the navigation table, there are literally billions of fractionalized electrode configurations that can be selected. However, due to memory and time constraints, only a limited number of fractionalized electrode configurations are stored within the navigation table. Therefore, not every desired electrode combination and associated fractionalized current values can be represented within a steering table.

Furthermore, a substantial amount of time and effort must be spent in developing navigation tables for each new lead design, thereby presenting a bottleneck for lead development. For example, each steering table must take into account the variability in electrode position or stimulation input. The variability in electrode position may be due to, e.g., a different lead model, different lead configurations (e.g., a closely spaced side-by-side configuration, a closely spaced top-bottom configuration, a widely spaced top-bottom configuration, or a widely spaced side-by-side configuration), stagger of the leads, etc. The variability in stimulation input may be due to, e.g., the development or inclusion of additional steerable fields (e.g., medio-lateral tripole steering), upgrades in steering controls (e.g., focusing/blurring of fields, anode intensification or de-intensification (i.e., increasing or decreasing local anodic current relative to cathodic current), current steering from different screens, etc. Because the implementation of new navigation tables must take into account all leads that are to be used with the IPG, as well as the different lead positions, this challenge slows the ability to include new navigation features in the system.

Furthermore, if the remote control needs to be reprogrammed; for example, if the patient returns to a physician's office to be refitted to improve the stimulation therapy provided by the neurostimulator, the clinician may have to start the fitting from scratch. In particular, while the remote control is capable of uploading the stimulation parameter sets to the Bionic Navigator® to aid in reprogramming the remote control, they may be different from any stimulation parameter sets that are capable of being generated using the navigation table due to the limited number of fractionalized electrode configurations within the navigation table; that is, the fractionalized electrode configurations currently stored in the remote control may not match any fractionalized electrode configurations stored in the navigation table because they were originally generated when the Bionic Navigator® was operated in the manual mode.

In any event, if the stimulation parameter sets uploaded from the remote control to the Bionic Navigator® do not identically match any stimulation parameter set corresponding to a fractionalized electrode configuration stored in the navigation table, it cannot be used as a starting point in reprogramming the remote control/IPG. As a result, the amount of time required to reprogram the remote control/IPG may be as long as the amount of time required to originally program the remote control/IPG with the Bionic Navigator®. Because programming the remote control can be quite complex, even when the Bionic Navigator® is operated in the navigation mode, the time lost as a result of having to reprogram the remote control/IPG from scratch, can be quite significant.

There, thus, remains a need for an improved method and system for steering electrical current between lead electrodes.

SUMMARY OF THE INVENTION

In accordance with a first aspect of the present inventions, a system for an electrical neurostimulator coupled to a plurality of electrodes is provided. The system comprises a processor configured for defining a target current source multipole (e.g., a target bipole or a target tripole) relative to the plurality of electrodes, and emulating the target multipole by defining an initial electrical current distribution for the electrodes, such that a first set of active electrodes respectively has electrical current values (e.g., fractionalized electrical current values) of a first polarity, and a second set of active electrodes respectively has electrical current values of a second polarity. The processor is further configured for comparing each of the electrical current values of the first polarity to a first threshold value, and zeroing-out at least one of the electrodes in the first active electrode set based on the comparison.

In one embodiment, the first threshold value is an absolute threshold electrical current value, in which case, the electrical current value of each of the zero-out electrode(s) in the first active electrode set is less than the absolute threshold electrical current value. In another embodiment, the first threshold value is a standard deviation threshold value less than the highest electrical current value of the first polarity, in which case, the electrical current value of each of the zeroed-out electrodes in the first active electrode set may be less than the standard deviation threshold value.

The processor is further configured for redistributing the electrical current value of each of the at least one zeroed-out electrode in the first active electrode set to remaining ones of the electrodes in the first active electrode set to define a new electrical current distribution for the electrodes. In one embodiment, the processor is configured for redistributing the electrical current value of each of the zeroed-out electrode(s) in the first active electrode set to the remaining electrodes in the first active electrode set in proportion to the electrical current values of the remaining electrodes in the first active electrode set.

In one embodiment, the processor is further configured for comparing each of the electrical current values of the second polarity to a second threshold value (which may be equal to the first threshold value), zeroing-out at least one of the electrodes in the second active electrode set based on the comparison, and redistributing the electrical current value of each of the zeroed-out electrode(s) in the second active electrode set to remaining ones of the electrodes in the second active electrode set to define the new electrical current distribution for the electrodes.

The system further comprises a controller configured for instructing the electrical neurostimulator to convey electrical current to the plurality of electrodes in accordance with the new electrical current distribution. In an optional embodiment, the system further comprises telemetry circuitry, in which case, the controller may be further configured for instructing the electrical neurostimulator via the telemetry circuitry. In another optional embodiment, the system further comprises a housing containing the processor and controller.

In accordance with a second aspect of the present inventions, a method of providing therapy to a patient using a plurality of electrodes implanted within the patient is provided. The method comprises defining a target current source multipole (e.g., a target bipole or a target tripole) relative to the plurality of electrodes. The method further comprises emulating the target multipole by defining an initial electrical current distribution for the electrodes, such that a first set of active electrodes respectively has electrical current values (e.g., fractionalized electrical current values) of a first polarity, and a second set of active electrodes respectively has electrical current values of a second polarity. The method further comprises comparing each of the electrical current values of the first polarity to a first threshold value, and zeroing-out at least one of the electrodes in the first active electrode set based on the comparison.

In one method, the first threshold value is an absolute threshold electrical current value, in which case, the electrical current value of each of the zero-out electrode(s) in the first active electrode set is less than the absolute threshold electrical current value. In another method, the first threshold value is a standard deviation threshold value less than the highest electrical current value of the first polarity, in which case, the electrical current value of each of the zeroed-out electrodes in the first active electrode set may be less than the standard deviation threshold value.

The method further comprises redistributing the electrical current value of each of the at least one zeroed-out electrode in the first active electrode set to remaining ones of the electrodes in the first active electrode set to define a new electrical current distribution for the electrodes. In one method, the electrical current value of each of the zeroed-out electrode(s) in the first active electrode set is redistributed to the remaining electrodes in the first active electrode set in proportion to the electrical current values of the remaining electrodes in the first active electrode set.

One method further comprises comparing each of the electrical current values of the second polarity to a second threshold value (which may be equal to the first threshold value), zeroing-out at least one of the electrodes in the second active electrode set based on the comparison, and redistributing the electrical current value of each of the at least one zeroed-out electrode in the second active electrode set to remaining ones of the electrodes in the second active electrode set to define the new electrical current distribution for the electrodes.

The method further comprises conveying electrical current to the plurality of electrodes in accordance with the new electrical current distribution, thereby providing the therapy.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

Appendix A is an exemplary navigation table containing different fractionalized electrode combinations that can be used in a Spinal Cord Stimulation (SCS) system;

FIG. 9A-9C are views constituent current sources located at four different electrodes of an electrode array that the software program of FIG. 7 can use to map the ideal electrical fields onto the electrodes;

FIG. 10 is a transfer matrix used by the software program of FIG. 7 to compute the relative strengths of the constituent current sources needed to match the ideal electrical field at the spatial observation points;

FIG. 11 is a diagram illustrating the unit constituent current sources of FIGS. 9A-9C mapped onto the four exemplary electrodes;

FIGS. 12A-12E are electrical current distributions computed by the software program of FIG. 7, as realized in a Matlab program, for various electrode configurations;

FIGS. 14A and 14B are other electrical current distributions computed by the software program of FIG. 7 prior to using a "cleaning" algorithm and after using the "cleaning" algorithm.

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
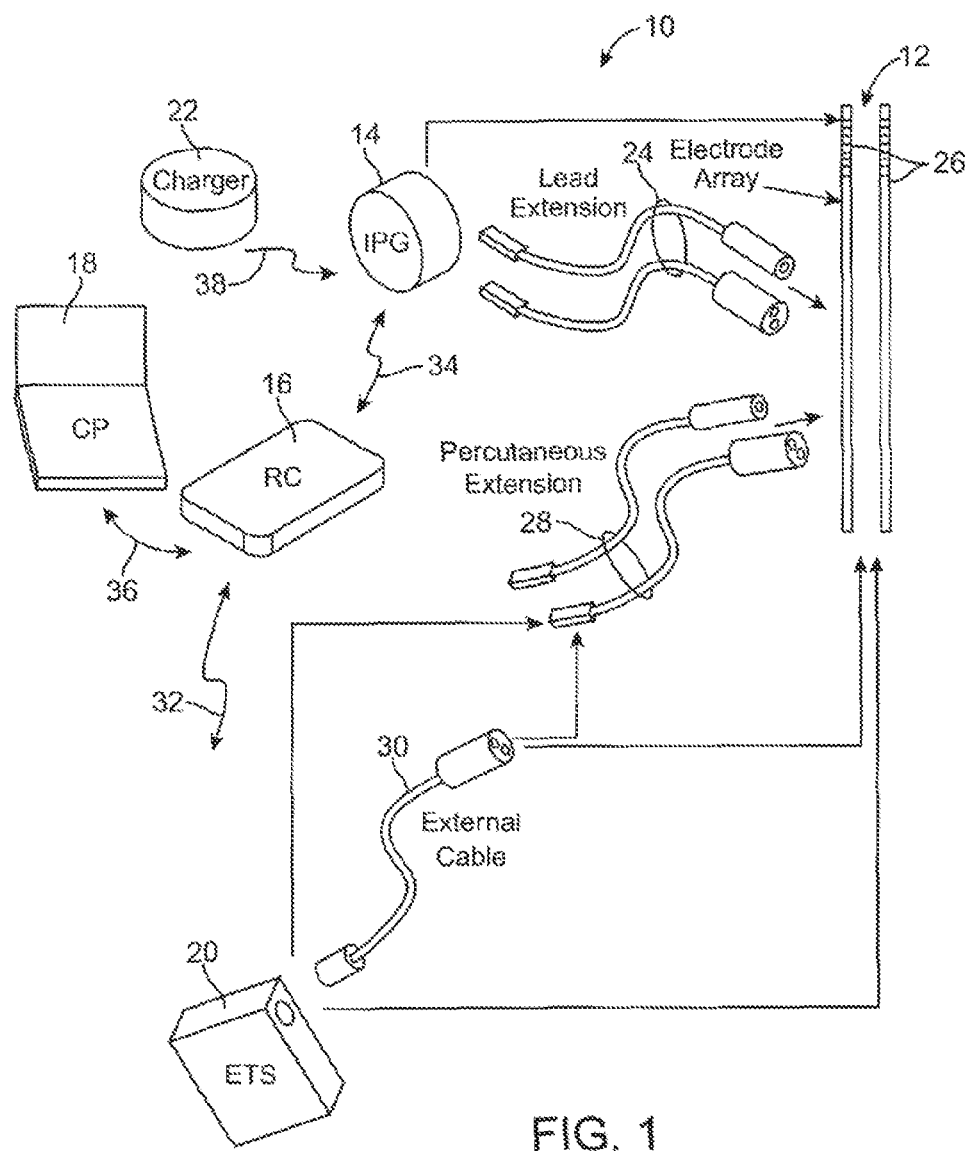
FIG. 1 is perspective view of one embodiment of a SCS system arranged in accordance with the present inventions.

Turning first to FIG. 1, an exemplary SCS system 10 generally includes one or more (in this case, two) implantable stimulation leads 12, an implantable pulse generator (IPG) 14, an external remote controller RC 16, a clinician's programmer (CP) 18, an External Trial Stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 are arranged in-line along the stimulation leads 12. In alternative embodiments, the electrodes 26 may be arranged in a two-dimensional pattern on a single paddle lead. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
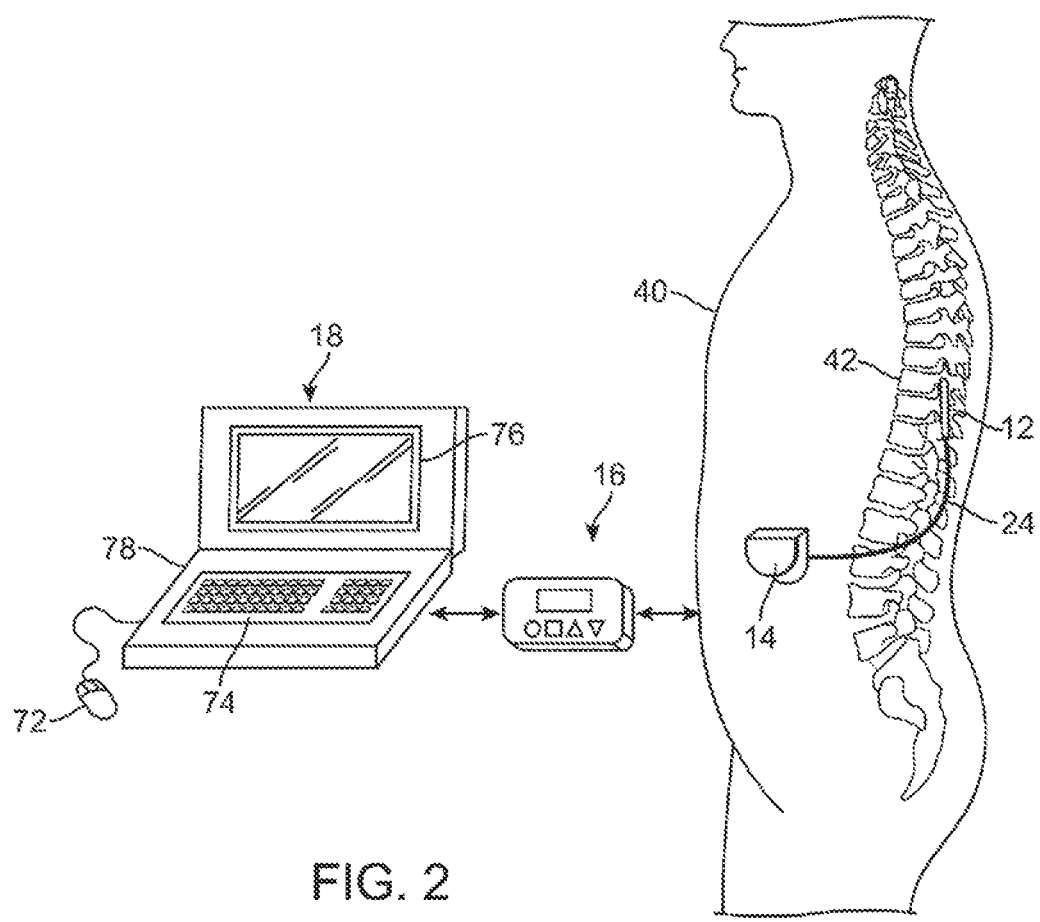
FIG. 2 is a plan view of the SCS system of FIG. 2 in use with a patient.

As shown in FIG. 2, the electrode leads 12 are implanted within the spinal column 42 of a patient 40. The preferred placement of the electrode leads 12 is adjacent, i.e., resting upon, the dura near the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12. As there shown, the CP 18 communicates with the IPG 14 via the RC 16.

Figure 3:
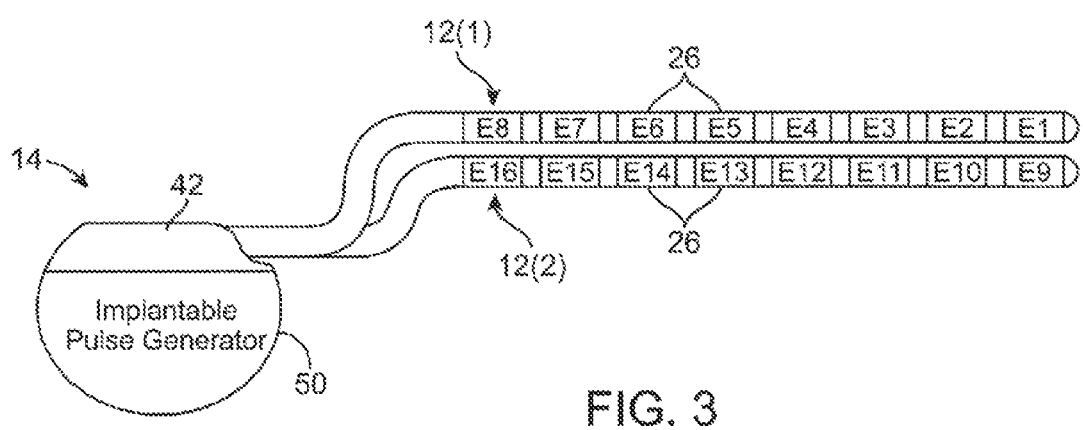
FIG. 3 is a side view of an implantable pulse generator and a pair of stimulation leads that can be used in the SCS system of FIG. 1.

Referring now to FIG. 3, the external features of the stimulation leads 12 and the IPG 14 will be briefly described. One of the stimulation leads 12 has eight electrodes 26 (labeled E1-E8), and the other stimulation lead 12 has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the stimulation leads 12 mates in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

The IPG 14 may be configured for conveying sub-threshold electrical signals between the lead electrodes 26 in order to take electrical measurements (e.g., impedance and/or field potential measurements). Such measurements can be used to determine the relative location and/or orientation of the leads 12 (e.g., lateral spacing between the leads or longitudinal stagger between the leads, tilt angle between leads), and thus, the relative locations between the electrodes 26. Further details discussing techniques used to determine relative lead locations/orientations are described in U.S. application Ser. No. 10/310,202, entitled "Apparatus and Method for Determining the Relative position and Orientation of Neurostimulation Leads, and U.S. application Ser. No. 11/096,483, entitled "Apparatus and Methods for Detecting Position of Neurostimulation Leads," which are expressly incorporated herein by reference.

It should be noted that rather than an IPG, the SCS system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 4:
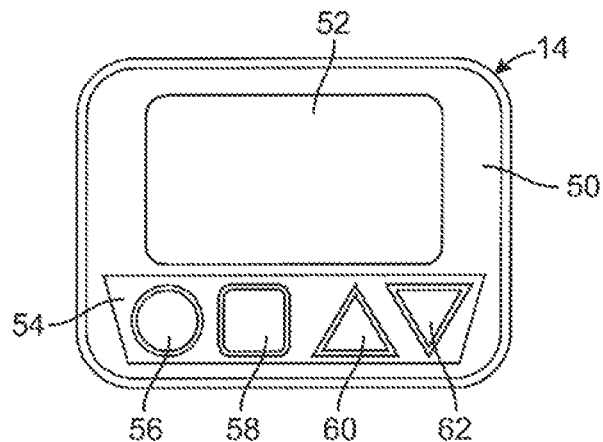
FIG. 4 is a plan view of a remote control that can be used in the SCS system of FIG. 1.

Referring now to FIG. 4, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touchscreen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14ON and OFF. The button 58 serves as a select button that allows the RC 16 to switch between screen displays and/or parameters. The buttons 60 and 62 serve as up/down buttons that can actuated to increment or decrement any of stimulation parameters of the pulse generated by the IPG 14, including pulse amplitude, pulse width, and pulse rate. For example, the selection button 58 can be actuated to place the RC 16 in an "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 5:
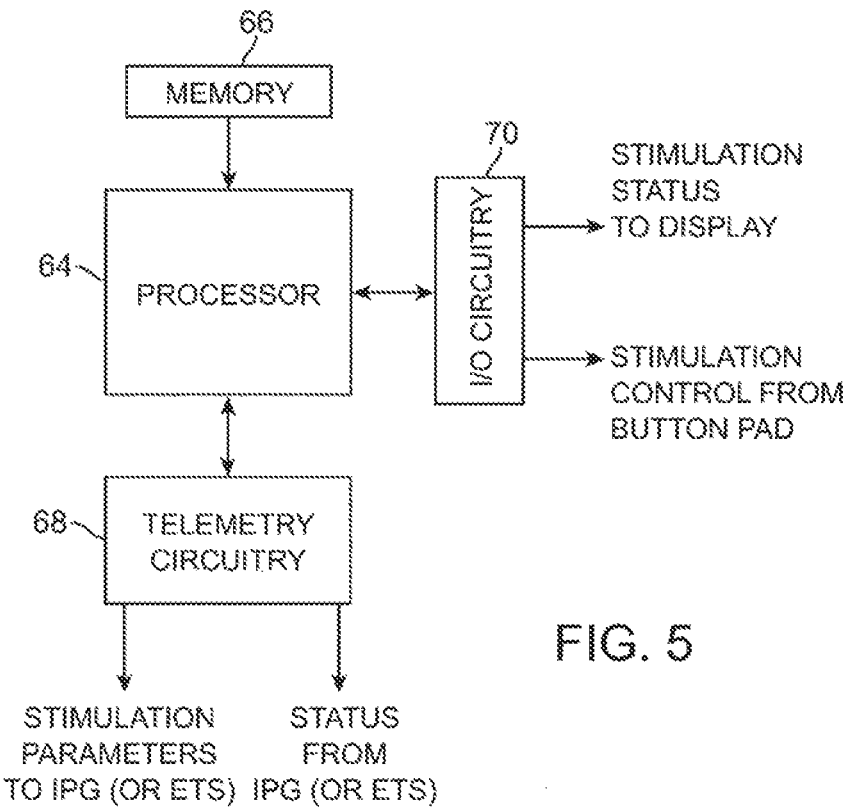
FIG. 5 is a block diagram of the internal componentry of the remote control of FIG. 4.

Referring to FIG. 5, the internal components of an exemplary RC 16 will now be described. The RC 16 generally includes a processor 64 (e.g., a microcontroller), memory 66 that stores an operating program for execution by the processor 64, as well as stimulation parameter sets in a look-up table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 4). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 (or ETS 20) via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 near the spinal cord.

As shown in FIG. 2, the overall appearance of the CP 18 is that of a laptop personal computer (PC), and in fact, may be implanted using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 (or ETS 20) to allow the optimum stimulation parameters to be determined based on patient feedback and for subsequently programming the IPG 14 (or ETS 20) with the optimum stimulation parameters.

Figure 6:
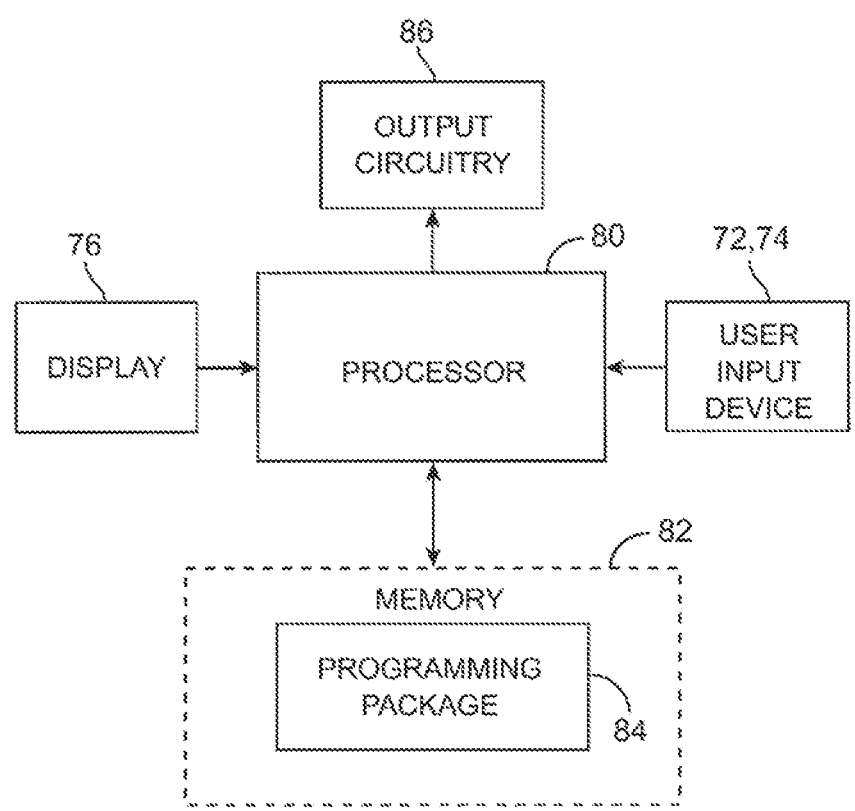
FIG. 6 is a block diagram of the components of a computerized programming system that can be used in the SCS system of FIG. 1.

To allow the clinician to perform these functions, the CP 18 includes a mouse 72, a keyboard 74, and a programming display screen 76 housed in a case 78. It is to be understood that in addition to, or in lieu of, the mouse 72, other directional programming devices may be used, such as a joystick, or directional keys included as part of the keys associated with the keyboard 74. As shown in FIG. 6, the CP 18 generally includes a processor 80 (e.g., a central processor unit (CPU)) and memory 82 that stores a stimulation programming package 84, which can be executed by the processor 80 to allow a clinician to program the IPG 14, and RC 16. The CP 18 further includes output circuitry 86 (e.g., via the telemetry circuitry of the RC 16) for downloading stimulation parameters to the IPG 14 and RC 16 and for uploading stimulation parameters already stored in the memory 66 of the RC 16, via the telemetry circuitry 68 of the RC 16, as well as obtaining status and measurement information from the IPG 14.

Significantly, in addition to providing conventional stimulation capability, the stimulation programming package 84 of the CP 18 can be executed to implement a navigation paradigm that mimics arbitrary electrical fields (e.g., a bipole with an arbitrary separation and/or arbitrary position relative to the electrode array 26), thereby de-linking the development of leads from substantial software changes (typically involving the development of new navigation tables) to expedite development of new technology (e.g., new leads, improved lead/electrode position/orientation detection, adaptors to competitor's leads). Although the execution of the stimulation programming package 84 is described as being executed in the CP 18 to implement the navigation paradigm, it should be appreciated that the programming package 84 may be executed in the RC 16 (although the processing power of the RC 16 may not be as great as that of the CP 18).

Figure 7:
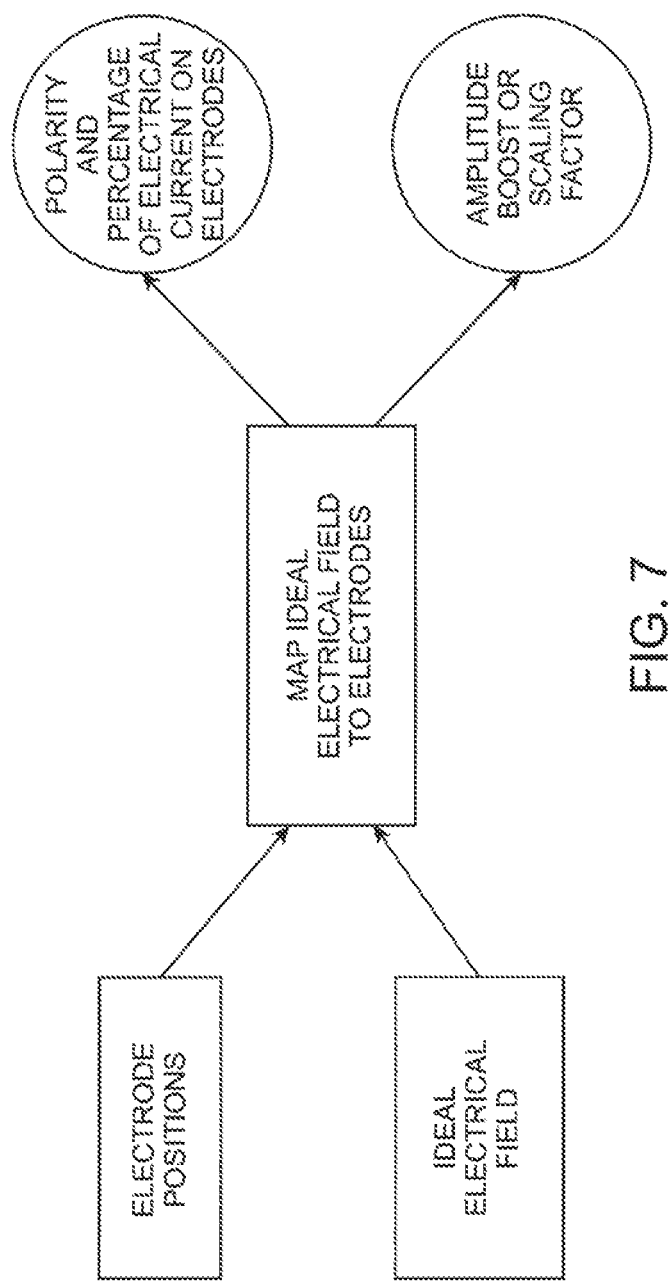
FIG. 7 is a block diagram illustrating an exemplary software program programmed into the clinician's programmer of the SCS system of FIG. 1 to map an ideal electrical field onto any electrode configuration.

With reference to FIG. 7, the CP 18 includes software that accepts relative electrode positions and a representation of an ideal electrical field (instead of including these parameters in the design of navigation tables) and maps the ideal electrical field to the electrodes, thereby yielding the polarities and percentages of electrical current to be associated with the electrodes, as well as a boost or scaling factor for globally adjusting the magnitude of the total current supplied to the electrodes to maintain a perceived intensity level of the electrical stimulation. It should be noted that this paradigm calls for the input of electrode locations and information about the desired electrical field independently, which is in contrast to the prior art paradigm, which uses navigation tables that are specific to a lead design and to electrode location information, the updating of which requires substantial effort and coding.

Figures 8A, 8B:
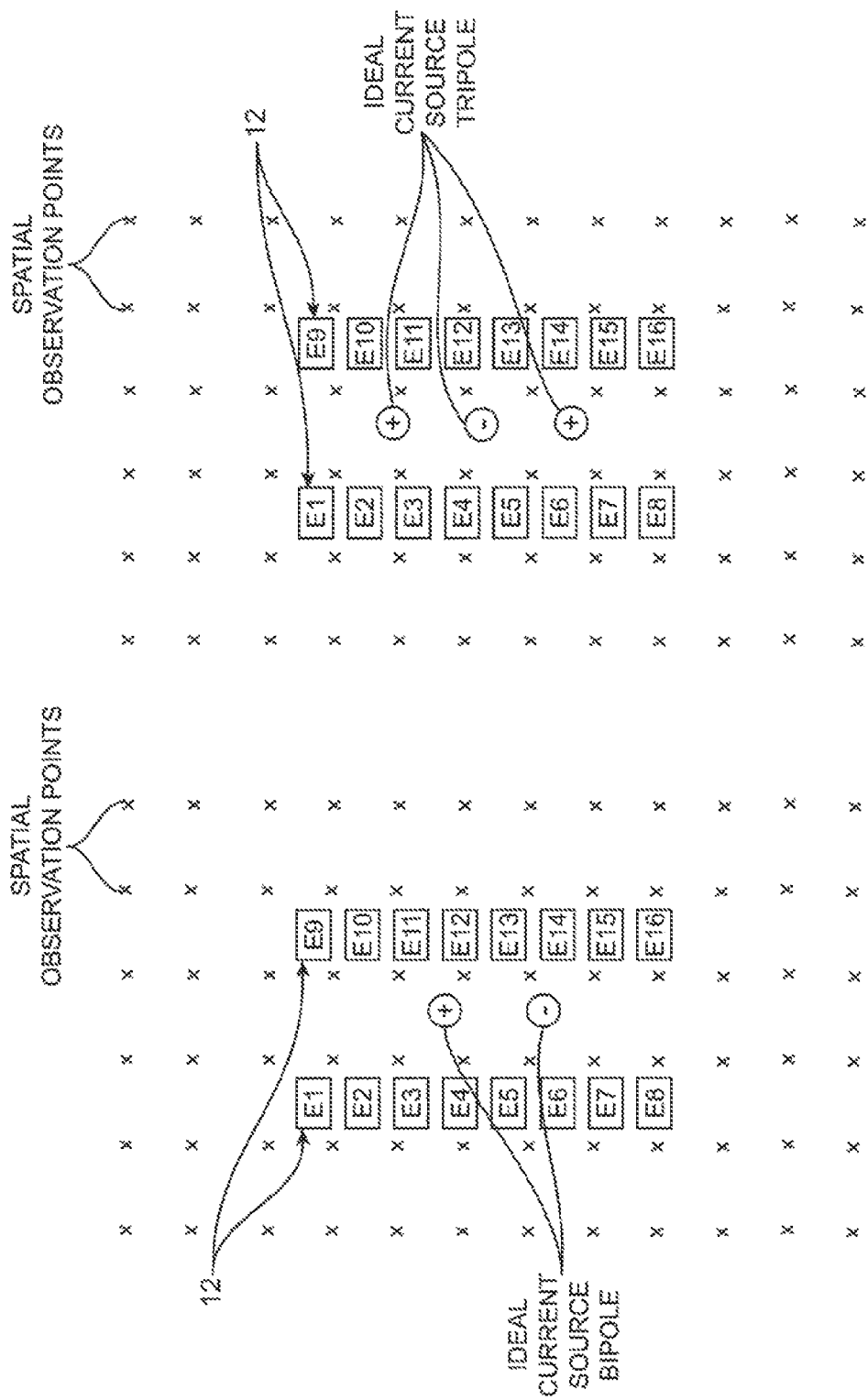
FIGS. 8A and 8B are views of ideal current sources located within an exemplary configuration of electrodes and spatial observation points at which the electrical field generated by the ideal current sources are measured.

The CP 18 maps the ideal electrical field to the electrode array by first estimating the field potential values (or some other linear electrical parameter, such as an activating function, current density, etc.) of the ideal field at a plurality of spatial observation points. Referring to FIGS. 8A and 8B, the CP 18 accomplishes this step by determining the desired locations of ideal current source poles relative to the electrode array 26, and modeling an electrical field generated by the ideal current source poles to determine desired field potential values at the spatial observation points (e.g., using analytical and/or numerical models). The ideal current source poles may form, e.g., a bipole (FIG. 8A) or a tripole (FIG. 8B). Although ideal current source poles are one way to represent an "ideal electrical field" or target field, other representations of target fields may be used.

The locations of the ideal current source poles may be determined in a manner that places the resulting electrical field over an identified region of the patient to be stimulated. Preferably, the spatial observation points are spaced in a manner that would, at the least, cover the entire tissue region to be stimulated and/or a tissue region that should not be stimulated. The locations of the ideal current source poles may be defined by the user, and may be displayed to the user along with the electrode locations, which as briefly discussed above, may be determined based on electrical measurements taken at the electrodes. For example, the ideal current source poles can be selected in a manual screen (e.g., by using a mouse to click around the electrode array), or the ideal current sources poles can be selected using a navigation screen (e.g., by steering the ideal current source poles around the electrodes using directional controls, such as by manipulating displayed arrow keys or by using a joystick). Further details describing the use of manual screens and navigation screens are set forth in U.S. Patent Application Ser. No. 61/080,187, entitled "System and Method for Converting Tissue Stimulation Programs in a Format Usable by an Electrical Current Navigator," which is expressly incorporated herein by reference.

Alternatively, the CP 18 may automatically determine the locations of the ideal current source poles, e.g., heuristically (e.g., cathodes (or anodes) located where stimulation is to occur or not to occur) or using a model-based evaluation (such as, e.g., an activating function fit). The number of spatial observation points should be selected to provide a reasonably accurate modeling of the ideal electrical field without requiring an inordinate amount of processing time and/or computer resources. For example, the number of spatial observation points may be proportional to the number of electrodes and may number on the order of several thousand.

Referring to FIGS. 9A-9C, the CP 18 then selects, or allows a user to select, a plurality of constituent current sources at the locations of the electrodes 26. As briefly discussed above, the locations of the electrodes can be determined based on measurements taken at the electrodes in response to sub-threshold electrical signals transmitted between the electrodes. Preferably, the constituent current sources are linearly independents. In the illustrated embodiment, bipoles are selected as constituent sources, because they are simple, and lend themselves well to conservation of current (i.e., if all constituent sources have conserved current (net zero), then any linear combination of them will also have conserved current). For example, a first constituent current source can be defined at the locations of electrodes E1 and E2 as −100% and +100%, respectively (FIG. 9A); a second constituent current source can be defined at the locations of electrodes E2 and E3 as −100% and +100%, respectively (FIG. 9B); a third constituent current source can be defined at the locations of electrodes E3 and E4 as −100% and +100%, respectively (FIG. 9C); and so on. Preferably, the location of each of the electrodes is included within at least one of the constituent sources. Thus, the minimum number of constituent sources may be equal to the number of contacts less one, or may equal the number of contacts (e.g., if a monopole is used as the constituent source).

Once the constituent sources are selected, the CP 18 determines the relative strengths of the constituent current sources that, when combined, result in estimated electrical field potential values at the spatial observation points that best matches the desired field potential values at the spatial observation points. In particular, the CP 18 models the constituent current sources (e.g., using analytical and/or numerical models) and estimates the field potential values per unit current (V/mA) generated by each of the constituent current sources at the spatial observation points, and generating an m×n transfer matrix (shown in FIG. 10) from the estimated field potential values per unit current, with m equaling the number of spatial observation points and n equaling the number of constituent sources. The relative strengths of the constituent current sources are determined using an optimization function that includes the transfer matrix A and the desired field potential values.

In the illustrated embodiment, the optimization function is a least-squares (over-determined) function expressed as: $|\phi - A\hat{j}|^2$, where $\phi$ is an m-element vector of the desired field potential values, A is the transfer matrix, and $\hat{j}$ is an n-element vector of the strengths of the constituent current sources. The constituent current source strengths $\hat{j}$ are solved such that the optimization function $|\phi - A\hat{j}|^2$ is minimized. It should be recognized that the square difference is minimized if $\phi = A\hat{j}$. One approach for solving this problem would be to invert the transfer matrix A and pre-multiply, such that $A^{-1}\phi = A^{-1}A\hat{j}$, which yields the solution $\hat{j} = A^{-1}\phi$.

Matrix inversions can be computationally expensive, which may not present a significant issue if the CP 18 has the necessary computational power. However, if the optimization function is to be solved in a less computationally powerful device, such as the RC 16, other more efficient methods for solving the least-squares problem may be desirable. For example, a QR factorization using Given's rotations can be used as disclosed in G. Golub & C. van Loan (1996), Matrix computations, Third Edition, The Johns Hopkins University Press, London. This method involves converting the transfer matrix A to QR matrices (Q is an orthogonal matrix, and R is an upper triangular matrix). Thus, the equation $\phi = A\hat{j}$ becomes $\phi = QR\hat{j}$, which can be pre-multiplied by the transpose of the orthogonal matrix Q, such that $Q^T\phi = Q^TQR\hat{j}$. This yields the equation $Q^T\phi = R\hat{j}$. Because R is an upper triangular matrix, the solution for the constituent current source strengths $\hat{j}$ is straight forward.

Once the strengths of the constituent current sources are determined, the CP 18 converts these strengths to current distributions on the electrodes in the form of a polarity and percentage. This can be accomplishing using the equation:

$$I_e = \sum_{i=1}^{n} \hat{j}_i x c_{i(e)},$$

where e is the specific electrode index, $I_e$ is the percentage and polarity of the electrical current on electrode $E_n$, i is the specific constituent source index, n is the number of constituent sources, and $c_{i(e)}$ is the unit vector pole (+1 or −1) of the specific constitute source $c_i$ at the location of specific electrode e.

For example, FIG. 11 shows three constituent sources $c_1$, $c_2$, $c_3$ (equal to the number of electrodes less one), with the first constituent source $c_1$ (−1, 1) being defined at the locations of electrodes E1, E2, the second constituent source $c_2$ (−1, 1) being defined at the locations of electrodes E2, E3, and the third constituent source $c_3$ (−1, 1) being defined at the locations of electrodes E3, E4. Assuming that the strengths of the constituent sources are determined in accordance with the vector $$\hat{j} = \begin{vmatrix} \hat{j}_1 \\ \hat{j}_2 \\ \hat{j}_3 \end{vmatrix} = \begin{vmatrix} +2 \\ -1 \\ +3 \end{vmatrix},$$

then the polarity and percentage of the electrical current on each of the electrodes E1-E4 can respectively be determined as follows:

$$I_1 = \sum_{i=1}^{n} \hat{j}_i x c_{i(e)} = \hat{j}_1 x c_{1(1)} + \hat{j}_2 x c_{2(1)} + \hat{j}_3 x c_{3(1)} =$$

$$(2) \times (-1) + (-1) \times (0) + (3) \times (0) = -2 = -33\%;$$

$$I_2 = \sum_{i=1}^{n} \hat{j}_i x c_{i(e)} = \hat{j}_1 x c_{1(2)} + \hat{j}_2 x c_{2(2)} + \hat{j}_3 x c_{3(2)} =$$

$$(2) \times (1) + (-1) \times (-1) + (3) \times (0) = 3 = 50\%;$$

$$I_3 = \sum_{i=1}^{n} \hat{j}_i x c_{i(e)} = \hat{j}_1 x c_{1(3)} + \hat{j}_2 x c_{2(3)} + \hat{j}_3 x c_{3(3)} =$$

$$(2) \times (0) + (-1) \times (1) + (3) \times (-1) = -4 = -67\%;$$

$$I_4 = \sum_{i=1}^{n} \hat{j}_i x c_{i(e)} = \hat{j}_1 x c_{1(4)} + \hat{j}_2 x c_{2(4)} + \hat{j}_3 x c_{3(4)} =$$

$$(2) \times (0) + (-1) \times (0) + (3) \times (1) = 3 = 50\%.$$

It should be noted that, due to the conservation of current, the sum of the currents $I_1$-$I_4$ equals zero. The CP 18 may globally scale the magnitude of the currents $I_1$-$I_4$ up or down to achieve the desired therapeutic effect.

Referring to FIGS. 12A-12E, the afore-described optimization paradigm was implement using a Matlab computer program to test different ideal electrical fields with respect to different electrode configurations intended to be implanted adjacent the spinal cord of a patient. The electrical fields can either be considered to be a rostro-caudal electrical field (i.e., current source poles arranged longitudinally up and down along the spinal cord) or a medio-lateral electrical field (i.e., current sources poles arranged transversely across the spinal cord).

Figures 12A, 12B:
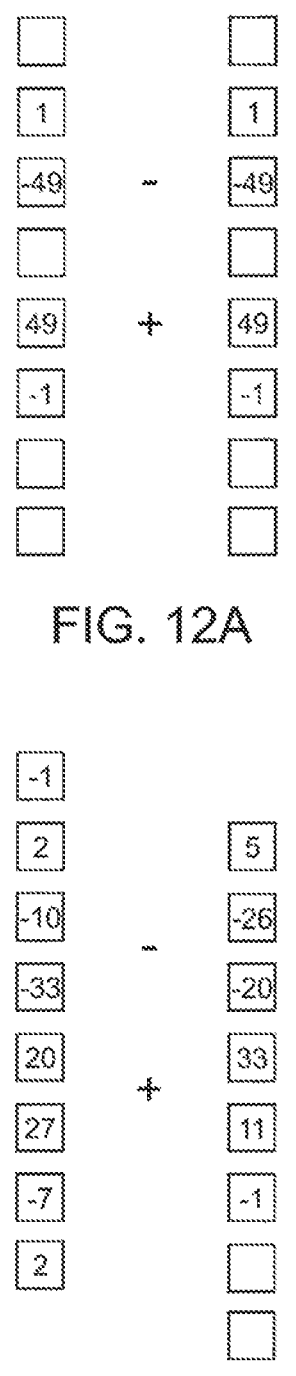

Referring to FIG. 12A, a target current source bipole was modeled to generate an ideal rostro-caudal electrical field between two non-staggered columns of electrodes each, and the resulting ideal electrical field was mapped onto the electrodes. As there shown, almost all of the cathodic electrical current has been assigned to two electrodes immediately adjacent to the cathode of the target bipole, and almost all of the anodic electrical current has been assigned to two electrodes immediately adjacent to the anode of the target bipole. The location of the target bipole can be steered (or otherwise selected) up, down, left, or right relative to the electrode arrays, such that (1) as the simple target bipole moves up in the electrode array, the assigned cathodic and anodic electrical current will be shifted up in the electrode array; (2) as the simple target bipole moves down in the electrode array, the assigned cathodic and anodic electrical current will be shifted down in the electrode array; (3) as the simple target bipole moves left in the electrode array, the assigned cathodic and anodic electrical current will be shifted to the left side of the electrode array; and (4) as the simple target bipole moves right in the electrode array, the assigned cathodic and anodic electrical current will be shifted down in the electrode array.

Referring to FIG. 12B, a target current source bipole was modeled to generate an ideal rostro-caudal electrical field between two staggered columns of electrodes, and the resulting electrical field was mapped onto the electrodes. As there shown, the stagger between the electrode columns has caused the cathodic electrical current to be mainly distributed between two electrodes on the left side of the array (i.e., electrodes E3, E4) and two electrodes on the right side of the array (i.e., electrodes E9, E10), and the anodic electrical current to be mainly distributed between two electrodes on the left side of the array (i.e., electrodes E5, E6) and two electrodes on the right side of the array (i.e., electrodes E12, E13). Significantly, as opposed to the prior art current steering paradigm, which required different navigation tables for different lead staggers, the inventive current steering paradigm disclosed herein automatically takes the lead stagger into account when assigning the electrical current to the electrodes.

Figure 12C:
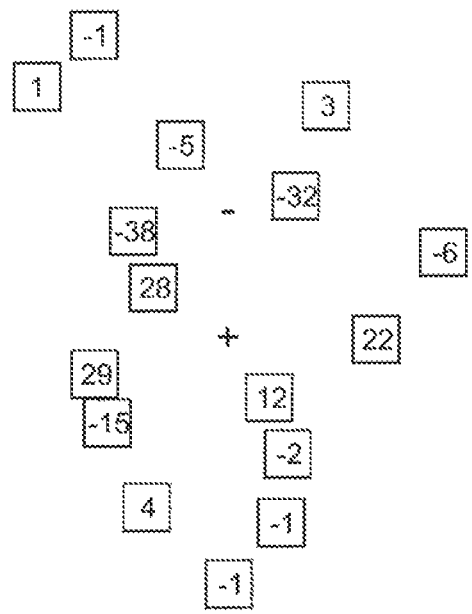

Referring to FIG. 12C, a target current source bipole was modeled to generate an ideal rostro-caudal electrical field among an arbitrary configuration of sixteen electrodes, and the resulting electrical field was mapped onto the electrodes. Significantly, in contrast to the prior art current steering paradigm, which is simply not capable of generating navigation tables for any arbitrary electrode configuration, the inventive current steering paradigm disclosed herein automatically takes into account any arbitrary electrode configuration when assigning the electrical current to the electrodes.

Figure 12D:

Referring to FIG. 12D, a target current source bipole with a relatively tight offset between the cathode and anode was modeled to generate an ideal rostro-caudal electrical field centered in the middle of a column of eight electrodes, and the resulting electrical field was mapped onto the electrodes. Thus, although the poles of the target bipole are quite close together and are placed in the middle of the electrode column, the inventive current steering paradigm is capable of properly assigning cathodic and anodic electrical current to the electrodes to mimic the desired electrical field.

Figure 12E:
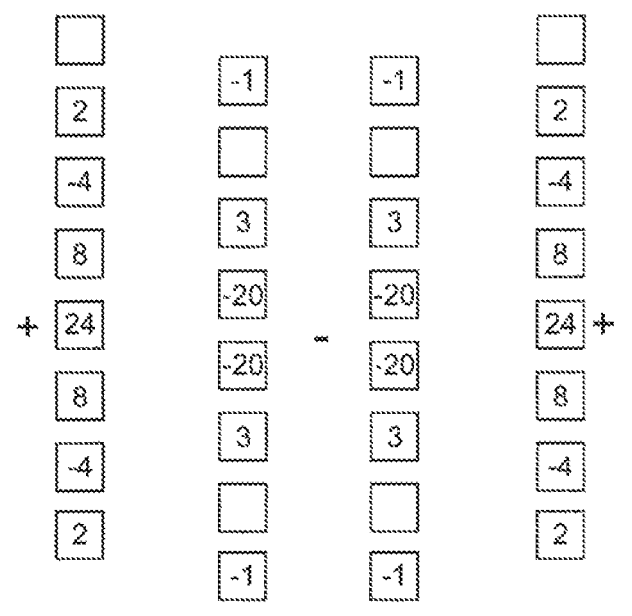

Referring to FIG. 12E, a target current source tripole was modeled to generate an ideal medio-lateral electrical field across four columns of electrodes, and the resulting electrical field was mapped onto the electrodes. As there shown, almost all of the cathodic current has been assigned to four electrodes within the two inner columns immediately adjacent to the cathode of the target tripole, and almost all of the anodic electrical current has been assigned to the electrodes on the outer columns immediately adjacent to the respective anodes of the target tripole.

It is expected that, when a relatively large number of electrodes are utilized, small insignificant currents (e.g., 1% or 2%) may be selected for certain electrodes. These small currents scattered on the electrode array reduce the efficiency of the system, because higher stimulation currents are required. Furthermore, if only electrode percentages are displayed to the user, the location of the stimulated region would not be as intuitive as other current steering methodologies. These efficiency and intuitiveness concerns may be addressed by introducing a "cleaning" algorithm, which may, e.g., be heuristic- or matrix-based, to post-process the optimized result.

Figure 13A:
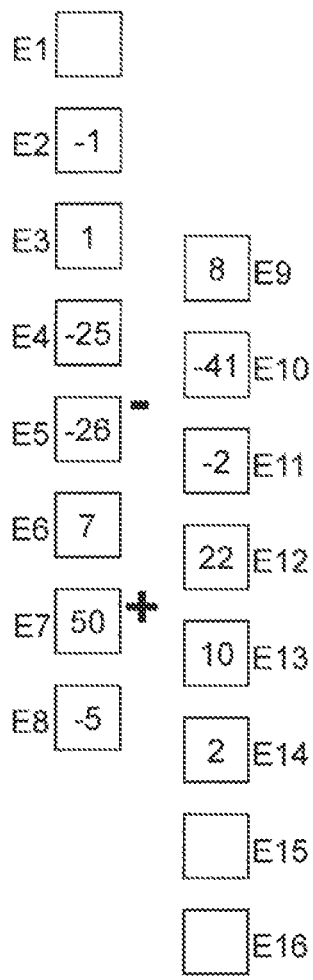
FIGS. 13A and 13B are electrical current distributions computed by the software program of FIG. 7 prior to using a "cleaning" algorithm and after using the "cleaning" algorithm.
Figure 13B:
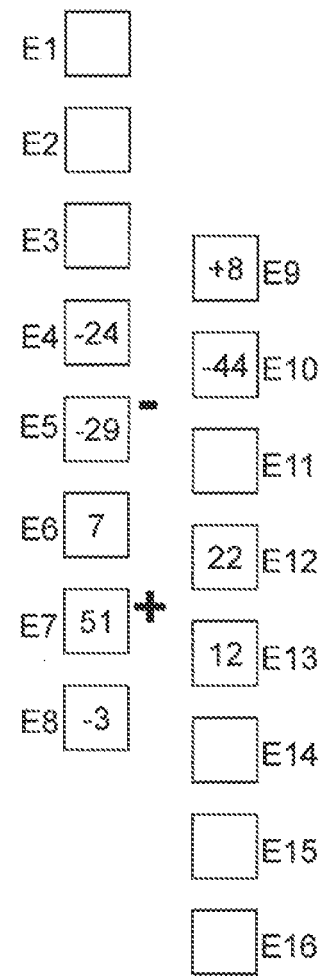

For example, an exemplary electrical current distribution determined using only an optimization algorithm is illustrated in FIG. 13A. As there shown, certain electrodes have currents of 1% or 2%. However, a cleaning algorithm may be utilized to "clean-up" some of the small currents, and in particular, to zero-out the 1% and 2% currents, as illustrated in FIG. 13B. As can be appreciated from FIG. 13B, the small currents that were zeroed-out are redistributed to the remaining electrodes having non-zero electrical currents (i.e., the active electrodes).

The cleaning algorithm described with respect to FIGS. 13A and 13B can best be described with respect to the method illustrated in FIG. 14. In particular, an ideal target current source multipole (e.g., a bipole or a tripole) relative to the plurality of electrodes can be defined, e.g., as shown in FIGS. 12A-12E (step 100). Next, an initial electrical current distribution for the electrodes 26 is defined in a manner that emulates the target multipole (step 102). The electrical current distribution that emulates the target multipole can be determined in the manner discussed above with respect to FIGS. 8-10. The initial electrical current distribution will naturally dictate that there be a cathodic set of active electrodes (i.e., cathodic electrodes having non-zero electrical current values), and an anodic set of active electrodes (i.e., anodic electrodes having non-zero electrical current values). For example, as shown in FIG. 13A, a cathodic set of electrodes encompassing electrodes E2, E4, E5, E8, E10, and E11, and the anodic set of electrodes encompassing electrodes E3, E6, E7, E9, and E14-E16 will emulate the illustrated target bipole.

Next, each of the cathodic electrical current values are compared to a first threshold value, and each of the anodic electrical current values are compared to a second threshold value (step 104), and at least one of the electrodes in the cathodic electrode set is zeroed-out, and at least one of the electrodes in the anodic electrode set is zeroed out, based on the comparison (step 106). The first and second threshold values may be the same or may be different. In one embodiment, the threshold value is an absolute value (e.g., 3%). For example, all electrodes in FIG. 13A that have fractionalized current values of less than a threshold value of 3% have been zeroed out. That is, electrodes E2, E3, E11, and E14, which respectively have fractionalized current values of −1%, 1%, −2%, and 2% (all less than 3%), have been zeroed out, as shown in FIG. 13B. In an alternative embodiment, the threshold value is not an absolute value, but rather varies in accordance with a function of the electrical current values. For example, for each electrode set, the threshold value may be a function of a standard deviation (e.g., 3 standard deviations) less than the highest electrical current value for that electrode set. Any electrode having an electrical current value that is less than this threshold value may be zeroed out.

Next, the electrical value of each of the electrodes that have been zeroed-out in the active cathodic electrode set or active anodic electrode set will be redistributed to the remaining electrodes in the respective active cathodic electrode set or active anodic electrode set to define a new electrical current distribution for the electrodes (step 108). For example, as shown in FIGS. 13A and 13B, the electrical current of cathodic electrodes E2 and E11 (FIG. 13A) has been redistributed to cathodic electrodes E4, E5, E8, and E10 (FIG. 13B), and the electrical current of anodic electrodes E3 and E14 (FIG. 13A) has been redistributed to anodic electrodes E6, E7, E9, E12, and E13 (FIG. 13B).

Figures 14A, 14B:
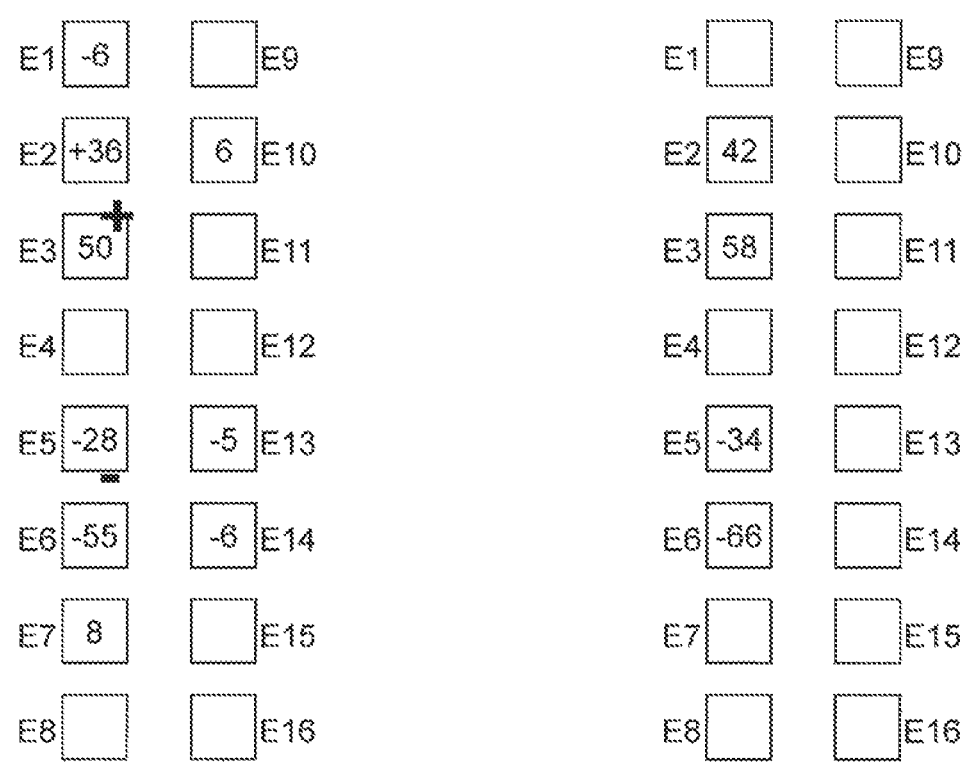

Optionally, the electrical value of each of the electrodes that have been zeroed-out in the active cathodic electrode set or active anodic electrode set will be redistributed in proportion to the electrical current values of the remaining electrodes in the respective active cathodic electrode set or active anodic electrode set. For example, as shown in FIG. 14A, electrodes E1, E7, E10, E13, and E14 have been zeroed out, and their electrical current values have been redistributed to electrodes E2, E3, E5, and E6 in proportion to the electrical current values of these electrodes, as shown in FIG. 14B.

In particular, the ratio of the electrical current value of anodic electrode E2 (36%) to the total electrical current for the remaining anodic electrodes (total of 86% for electrodes E2 and E3) is approximately 42%, and the ratio of the electrical current value of anodic electrode E2 (50%) to the total electrical current for the remaining anodic electrodes (total of 86% for electrodes E2 and E3) is approximately 58%. 14% of the anodic electrical current (8% for electrode E7 and 6% for electrode E10) will need to be redistributed to electrodes E2 and E3. 42% of the 14% anodic electrical current; that is 6% of the anodic electrical current, will be redistributed to electrode E2 (changes from 36% (FIG. 14A) to 42% (FIG. 14B)), and 58% of the 14% anodic electrical current; that is 8% of the anodic electrical current, will be redistributed to electrode E3 (changes from 50% (FIG. 14A) to 58% (FIG. 14B)).

The ratio of the electrical current value of cathodic electrode E5 (28%) to the total electrical current for the remaining cathodic electrodes (total of 83% for electrodes E5 and E6) is approximately 33%, and the ratio of the electrical current value of cathodic electrode E6 (55%) to the total electrical current for the remaining cathodic electrodes (total of 83% for electrodes E5 and E6) is approximately 67%. 17% of the cathodic electrical current (6% for electrode E1, 5% for electrode E13, and 6% for electrode E14) will need to be redistributed to electrodes E5 and E6. 33% of the 17% cathodic electrical current; that is 6% of the cathodic electrical current, will be redistributed to electrode E5 (changes from 28% (FIG. 14A) to 34% (FIG. 14B)), and 67% of the 17% anodic electrical current; that is 11% of the cathodic electrical current, will be redistributed to electrode E6 (changes from 55% (FIG. 14A) to 66% (FIG. 14B)).

After the electrical current is redistributed from the zeroed-out electrodes to the remaining active electrodes, the electrical current can be conveyed to the electrodes 26 in accordance with the new electrical current distribution (step 112).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

APPENDIX A

Simplified Steering Table

| Stim# | Electrode# | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| 1 | −1 | 0 | 0 | 0 | 0 | 0 | 0.5 | 0.5 | 0 | 0 | 0 | 0 | 0 | 0 | 0 | 0 |
| 2 | −1 | 0 | 0.05 | 0 | 0 | 0 | 0.45 | 0.5 | 0 | 0 | 0 | 0 | 0 | 0 | 0 | 0 |
| 3 | −1 | 0 | 0.1 | 0 | 0 | 0 | 0.4 | 0.5 | 0 | 0 | 0 | 0 | 0 | 0 | 0 | 0 |
| 4 | −1 | 0 | 0.15 | 0 | 0 | 0 | 0.4 | 0.45 | 0 | 0 | 0 | 0 | 0 | 0 | 0 | 0 |
| 5 | −1 | 0 | 0.2 | 0 | 0 | 0 | 0.4 | 0.4 | 0 | 0 | 0 | 0 | 0 | 0 | 0 | 0 |
| 6 | −1 | 0 | 0.25 | 0 | 0 | 0 | 0.35 | 0.4 | 0 | 0 | 0 | 0 | 0 | 0 | 0 | 0 |
| 7 | −1 | 0 | 0.3 | 0 | 0 | 0 | 0.3 | 0.4 | 0 | 0 | 0 | 0 | 0 | 0 | 0 | 0 |
| 8 | −1 | 0 | 0.35 | 0 | 0 | 0 | 0.3 | 0.35 | 0 | 0 | 0 | 0 | 0 | 0 | 0 | 0 |
| 9 | −1 | 0 | 0.4 | 0 | 0 | 0 | 0.3 | 0.3 | 0 | 0 | 0 | 0 | 0 | 0 | 0 | 0 |
| 10 | −1 | 0 | 0.45 | 0 | 0 | 0 | 0.25 | 0.3 | 0 | 0 | 0 | 0 | 0 | 0 | 0 | 0 |
| 11 | −1 | 0 | 0.5 | 0 | 0 | 0 | 0.2 | 0.3 | 0 | 0 | 0 | 0 | 0 | 0 | 0 | 0 |
| 12 | −1 | 0 | 0.55 | 0 | 0 | 0 | 0.2 | 0.25 | 0 | 0 | 0 | 0 | 0 | 0 | 0 | 0 |
| 13 | −1 | 0 | 0.6 | 0 | 0 | 0 | 0.2 | 0.2 | 0 | 0 | 0 | 0 | 0 | 0 | 0 | 0 |
| 14 | −1 | 0 | 0.65 | 0 | 0 | 0 | 0.15 | 0.2 | 0 | 0 | 0 | 0 | 0 | 0 | 0 | 0 |
| 15 | −1 | 0 | 0.7 | 0 | 0 | 0 | 0.1 | 0.2 | 0 | 0 | 0 | 0 | 0 | 0 | 0 | 0 |
| 16 | −1 | 0 | 0.75 | 0 | 0 | 0 | 0.1 | 0.15 | 0 | 0 | 0 | 0 | 0 | 0 | 0 | 0 |
| 17 | −1 | 0 | 0.8 | 0 | 0 | 0 | 0.1 | 0.1 | 0 | 0 | 0 | 0 | 0 | 0 | 0 | 0 |
| 18 | −1 | 0 | 0.85 | 0 | 0 | 0 | 0.05 | 0.1 | 0 | 0 | 0 | 0 | 0 | 0 | 0 | 0 |
| 19 | −1 | 0 | 0.9 | 0 | 0 | 0 | 0 | 0.1 | 0 | 0 | 0 | 0 | 0 | 0 | 0 | 0 |
| 20 | −1 | 0 | 0.95 | 0 | 0 | 0 | 0 | 0.05 | 0 | 0 | 0 | 0 | 0 | 0 | 0 | 0 |
| 21 | −1 | 0 | 1 | 0 | 0 | 0 | 0 | 0 | 0 | 0 | 0 | 0 | 0 | 0 | 0 | 0 |
| 22 | −1 | 0 | 0.95 | 0.05 | 0 | 0 | 0 | 0 | 0 | 0 | 0 | 0 | 0 | 0 | 0 | 0 |
| 23 | −1 | 0 | 0.9 | 0.1 | 0 | 0 | 0 | 0 | 0 | 0 | 0 | 0 | 0 | 0 | 0 | 0 |
| 24 | −1 | 0 | 0.85 | 0.15 | 0 | 0 | 0 | 0 | 0 | 0 | 0 | 0 | 0 | 0 | 0 | 0 |
| 25 | −1 | 0 | 0.8 | 0.2 | 0 | 0 | 0 | 0 | 0 | 0 | 0 | 0 | 0 | 0 | 0 | 0 |
| 26 | −1 | 0 | 0.75 | 0.25 | 0 | 0 | 0 | 0 | 0 | 0 | 0 | 0 | 0 | 0 | 0 | 0 |
| 27 | −1 | 0 | 0.7 | 0.3 | 0 | 0 | 0 | 0 | 0 | 0 | 0 | 0 | 0 | 0 | 0 | 0 |
| 28 | −1 | 0 | 0.65 | 0.35 | 0 | 0 | 0 | 0 | 0 | 0 | 0 | 0 | 0 | 0 | 0 | 0 |
| 29 | −1 | 0 | 0.6 | 0.4 | 0 | 0 | 0 | 0 | 0 | 0 | 0 | 0 | 0 | 0 | 0 | 0 |
| 30 | −1 | 0 | 0.55 | 0.45 | 0 | 0 | 0 | 0 | 0 | 0 | 0 | 0 | 0 | 0 | 0 | 0 |

APPENDIX A-continued

Simplified Steering Table

| Stim# | Electrode# | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| 31 | −1 | 0 | 0.5 | 0.5 | 0 | 0 | 0 | 0 | 0 | 0 | 0 | 0 | 0 | 0 | 0 | 0 |
| 32 | −1 | 0 | 0.45 | 0.55 | 0 | 0 | 0 | 0 | 0 | 0 | 0 | 0 | 0 | 0 | 0 | 0 |
| 33 | −1 | 0 | 0.4 | 0.6 | 0 | 0 | 0 | 0 | 0 | 0 | 0 | 0 | 0 | 0 | 0 | 0 |
| 34 | −1 | 0 | 0.35 | 0.65 | 0 | 0 | 0 | 0 | 0 | 0 | 0 | 0 | 0 | 0 | 0 | 0 |
| 35 | −1 | 0 | 0.3 | 0.7 | 0 | 0 | 0 | 0 | 0 | 0 | 0 | 0 | 0 | 0 | 0 | 0 |
| 36 | −1 | 0 | 0.25 | 0.75 | 0 | 0 | 0 | 0 | 0 | 0 | 0 | 0 | 0 | 0 | 0 | 0 |
| 37 | −1 | 0 | 0.2 | 0.8 | 0 | 0 | 0 | 0 | 0 | 0 | 0 | 0 | 0 | 0 | 0 | 0 |
| 38 | −1 | 0 | 0.15 | 0.85 | 0 | 0 | 0 | 0 | 0 | 0 | 0 | 0 | 0 | 0 | 0 | 0 |
| 39 | −1 | 0 | 0.1 | 0.9 | 0 | 0 | 0 | 0 | 0 | 0 | 0 | 0 | 0 | 0 | 0 | 0 |
| 40 | −1 | 0 | 0.05 | 0.95 | 0 | 0 | 0 | 0 | 0 | 0 | 0 | 0 | 0 | 0 | 0 | 0 |
| 41 | −1 | 0 | 0 | 1 | 0 | 0 | 0 | 0 | 0 | 0 | 0 | 0 | 0 | 0 | 0 | 0 |
| 42 | −0.95 | −0.05 | 0 | 0.95 | 0 | 0 | 0 | 0.05 | 0 | 0 | 0 | 0 | 0 | 0 | 0 | 0 |
| 43 | −0.9 | −0.1 | 0 | 0.9 | 0 | 0 | 0 | 0.1 | 0 | 0 | 0 | 0 | 0 | 0 | 0 | 0 |
| 44 | −0.85 | −0.15 | 0 | 0.85 | 0 | 0 | 0 | 0.15 | 0 | 0 | 0 | 0 | 0 | 0 | 0 | 0 |
| 45 | −0.8 | −0.2 | 0 | 0.8 | 0 | 0 | 0 | 0.2 | 0 | 0 | 0 | 0 | 0 | 0 | 0 | 0 |
| 46 | −0.75 | −0.25 | 0 | 0.75 | 0 | 0 | 0 | 0.25 | 0 | 0 | 0 | 0 | 0 | 0 | 0 | 0 |
| 47 | −0.7 | −0.3 | 0 | 0.7 | 0 | 0 | 0 | 0.3 | 0 | 0 | 0 | 0 | 0 | 0 | 0 | 0 |
| 48 | −0.65 | −0.35 | 0 | 0.65 | 0 | 0 | 0 | 0.35 | 0 | 0 | 0 | 0 | 0 | 0 | 0 | 0 |
| 49 | −0.6 | −0.4 | 0 | 0.6 | 0 | 0 | 0 | 0.4 | 0 | 0 | 0 | 0 | 0 | 0 | 0 | 0 |
| 50 | −0.55 | −0.45 | 0 | 0.55 | 0 | 0 | 0 | 0.45 | 0 | 0 | 0 | 0 | 0 | 0 | 0 | 0 |
| 51 | −0.5 | −0.5 | 0 | 0.5 | 0 | 0 | 0 | 0.5 | 0 | 0 | 0 | 0 | 0 | 0 | 0 | 0 |
| 52 | −0.45 | −0.55 | 0 | 0.45 | 0 | 0 | 0 | 0.55 | 0 | 0 | 0 | 0 | 0 | 0 | 0 | 0 |
| 53 | −0.4 | −0.6 | 0 | 0.4 | 0 | 0 | 0 | 0.6 | 0 | 0 | 0 | 0 | 0 | 0 | 0 | 0 |
| 54 | −0.35 | −0.65 | 0 | 0.35 | 0 | 0 | 0 | 0.65 | 0 | 0 | 0 | 0 | 0 | 0 | 0 | 0 |
| 55 | −0.3 | −0.7 | 0 | 0.3 | 0 | 0 | 0 | 0.7 | 0 | 0 | 0 | 0 | 0 | 0 | 0 | 0 |
| 56 | −0.25 | −0.75 | 0 | 0.25 | 0 | 0 | 0 | 0.75 | 0 | 0 | 0 | 0 | 0 | 0 | 0 | 0 |
| 57 | −0.2 | −0.8 | 0 | 0.2 | 0 | 0 | 0 | 0.8 | 0 | 0 | 0 | 0 | 0 | 0 | 0 | 0 |
| 58 | −0.15 | −0.85 | 0 | 0.15 | 0 | 0 | 0 | 0.85 | 0 | 0 | 0 | 0 | 0 | 0 | 0 | 0 |
| 59 | −0.1 | −0.9 | 0 | 0.1 | 0 | 0 | 0 | 0.9 | 0 | 0 | 0 | 0 | 0 | 0 | 0 | 0 |
| 60 | −0.05 | −0.95 | 0 | 0.05 | 0 | 0 | 0 | 0.95 | 0 | 0 | 0 | 0 | 0 | 0 | 0 | 0 |
| 61 | 0 | −1 | 0 | 0 | 0 | 0 | 0 | 1 | 0 | 0 | 0 | 0 | 0 | 0 | 0 | 0 |
| 62 | 0 | −1 | 0 | 0.05 | 0 | 0 | 0 | 0.95 | 0 | 0 | 0 | 0 | 0 | 0 | 0 | 0 |
| 63 | 0 | −1 | 0 | 0.1 | 0 | 0 | 0 | 0.9 | 0 | 0 | 0 | 0 | 0 | 0 | 0 | 0 |
| 64 | 0 | −1 | 0 | 0.15 | 0 | 0 | 0 | 0.85 | 0 | 0 | 0 | 0 | 0 | 0 | 0 | 0 |
| 65 | 0 | −1 | 0 | 0.2 | 0 | 0 | 0 | 0.8 | 0 | 0 | 0 | 0 | 0 | 0 | 0 | 0 |
| 66 | 0 | −1 | 0 | 0.25 | 0 | 0 | 0 | 0.75 | 0 | 0 | 0 | 0 | 0 | 0 | 0 | 0 |
| 67 | 0 | −1 | 0 | 0.3 | 0 | 0 | 0 | 0.7 | 0 | 0 | 0 | 0 | 0 | 0 | 0 | 0 |
| 68 | 0 | −1 | 0 | 0.35 | 0 | 0 | 0 | 0.65 | 0 | 0 | 0 | 0 | 0 | 0 | 0 | 0 |
| 69 | 0 | −1 | 0 | 0.4 | 0 | 0 | 0 | 0.6 | 0 | 0 | 0 | 0 | 0 | 0 | 0 | 0 |
| 70 | 0 | −1 | 0 | 0.45 | 0 | 0 | 0 | 0.55 | 0 | 0 | 0 | 0 | 0 | 0 | 0 | 0 |
| 71 | 0 | −1 | 0 | 0.5 | 0 | 0 | 0 | 0.5 | 0 | 0 | 0 | 0 | 0 | 0 | 0 | 0 |
| 72 | 0 | −1 | 0 | 0.55 | 0 | 0 | 0 | 0.45 | 0 | 0 | 0 | 0 | 0 | 0 | 0 | 0 |
| 73 | 0 | −1 | 0 | 0.6 | 0 | 0 | 0 | 0.4 | 0 | 0 | 0 | 0 | 0 | 0 | 0 | 0 |
| 74 | 0 | −1 | 0 | 0.65 | 0 | 0 | 0 | 0.35 | 0 | 0 | 0 | 0 | 0 | 0 | 0 | 0 |
| 75 | 0 | −1 | 0 | 0.7 | 0 | 0 | 0 | 0.3 | 0 | 0 | 0 | 0 | 0 | 0 | 0 | 0 |
| 76 | 0 | −1 | 0 | 0.75 | 0 | 0 | 0 | 0.25 | 0 | 0 | 0 | 0 | 0 | 0 | 0 | 0 |
| 77 | 0 | −1 | 0 | 0.8 | 0 | 0 | 0 | 0.2 | 0 | 0 | 0 | 0 | 0 | 0 | 0 | 0 |
| 78 | 0 | −1 | 0 | 0.85 | 0 | 0 | 0 | 0.15 | 0 | 0 | 0 | 0 | 0 | 0 | 0 | 0 |
| 79 | 0 | −1 | 0 | 0.9 | 0 | 0 | 0 | 0.1 | 0 | 0 | 0 | 0 | 0 | 0 | 0 | 0 |
| 80 | 0 | −1 | 0 | 0.95 | 0 | 0 | 0 | 0.05 | 0 | 0 | 0 | 0 | 0 | 0 | 0 | 0 |
| 81 | 0 | −1 | 0 | 1 | 0 | 0 | 0 | 0 | 0 | 0 | 0 | 0 | 0 | 0 | 0 | 0 |
| 82 | 0 | −1 | 0 | 0.95 | 0.05 | 0 | 0 | 0 | 0 | 0 | 0 | 0 | 0 | 0 | 0 | 0 |
| 83 | 0 | −1 | 0 | 0.9 | 0.1 | 0 | 0 | 0 | 0 | 0 | 0 | 0 | 0 | 0 | 0 | 0 |
| 84 | 0 | −1 | 0 | 0.85 | 0.15 | 0 | 0 | 0 | 0 | 0 | 0 | 0 | 0 | 0 | 0 | 0 |
| 85 | 0 | −1 | 0 | 0.8 | 0.2 | 0 | 0 | 0 | 0 | 0 | 0 | 0 | 0 | 0 | 0 | 0 |
| 86 | 0 | −1 | 0 | 0.75 | 0.25 | 0 | 0 | 0 | 0 | 0 | 0 | 0 | 0 | 0 | 0 | 0 |
| 87 | 0 | −1 | 0 | 0.7 | 0.3 | 0 | 0 | 0 | 0 | 0 | 0 | 0 | 0 | 0 | 0 | 0 |
| 88 | 0 | −1 | 0 | 0.65 | 0.35 | 0 | 0 | 0 | 0 | 0 | 0 | 0 | 0 | 0 | 0 | 0 |
| 89 | 0 | −1 | 0 | 0.6 | 0.4 | 0 | 0 | 0 | 0 | 0 | 0 | 0 | 0 | 0 | 0 | 0 |
| 90 | 0 | −1 | 0 | 0.55 | 0.45 | 0 | 0 | 0 | 0 | 0 | 0 | 0 | 0 | 0 | 0 | 0 |
| 91 | 0 | −1 | 0 | 0.5 | 0.5 | 0 | 0 | 0 | 0 | 0 | 0 | 0 | 0 | 0 | 0 | 0 |
| 92 | 0 | −1 | 0 | 0.45 | 0.55 | 0 | 0 | 0 | 0 | 0 | 0 | 0 | 0 | 0 | 0 | 0 |
| 93 | 0 | −1 | 0 | 0.4 | 0.6 | 0 | 0 | 0 | 0 | 0 | 0 | 0 | 0 | 0 | 0 | 0 |
| 94 | 0 | −1 | 0 | 0.35 | 0.65 | 0 | 0 | 0 | 0 | 0 | 0 | 0 | 0 | 0 | 0 | 0 |
| 95 | 0 | −1 | 0 | 0.3 | 0.7 | 0 | 0 | 0 | 0 | 0 | 0 | 0 | 0 | 0 | 0 | 0 |
| 96 | 0 | −1 | 0 | 0.25 | 0.75 | 0 | 0 | 0 | 0 | 0 | 0 | 0 | 0 | 0 | 0 | 0 |
| 97 | 0 | −1 | 0 | 0.2 | 0.8 | 0 | 0 | 0 | 0 | 0 | 0 | 0 | 0 | 0 | 0 | 0 |
| 98 | 0 | −1 | 0 | 0.15 | 0.85 | 0 | 0 | 0 | 0 | 0 | 0 | 0 | 0 | 0 | 0 | 0 |
| 99 | 0 | −1 | 0 | 0.1 | 0.9 | 0 | 0 | 0 | 0 | 0 | 0 | 0 | 0 | 0 | 0 | 0 |
| 100 | 0 | −1 | 0 | 0.05 | 0.95 | 0 | 0 | 0 | 0 | 0 | 0 | 0 | 0 | 0 | 0 | 0 |
| 101 | 0 | −1 | 0 | 0 | 1 | 0 | 0 | 0 | 0 | 0 | 0 | 0 | 0 | 0 | 0 | 0 |
| 102 | 0 | −0.95 | −0.05 | 0 | 0.95 | 0 | 0 | 0.05 | 0 | 0 | 0 | 0 | 0 | 0 | 0 | 0 |
| 103 | 0 | −0.9 | −0.1 | 0 | 0.9 | 0 | 0 | 0.1 | 0 | 0 | 0 | 0 | 0 | 0 | 0 | 0 |
| 104 | 0 | −0.85 | −0.15 | 0 | 0.85 | 0 | 0 | 0.15 | 0 | 0 | 0 | 0 | 0 | 0 | 0 | 0 |

APPENDIX A-continued

Simplified Steering Table

| | Electrode# | | | | | | | | | | | | | | | |
|---|---|---|---|---|---|---|---|---|---|---|---|---|---|---|---|---|
| Stim# | 1 | 2 | 3 | 4 | 5 | 6 | 7 | 8 | 9 | 10 | 11 | 12 | 13 | 14 | 15 | 16 |
| 105 | 0 | −0.8 | −0.2 | 0 | 0.8 | 0 | 0 | 0.2 | 0 | 0 | 0 | 0 | 0 | 0 | 0 | 0 |
| 106 | 0 | −0.75 | −0.25 | 0 | 0.75 | 0 | 0 | 0.25 | 0 | 0 | 0 | 0 | 0 | 0 | 0 | 0 |
| 107 | 0 | −0.7 | −0.3 | 0 | 0.7 | 0 | 0 | 0.3 | 0 | 0 | 0 | 0 | 0 | 0 | 0 | 0 |
| 108 | 0 | −0.65 | −0.35 | 0 | 0.65 | 0 | 0 | 0.35 | 0 | 0 | 0 | 0 | 0 | 0 | 0 | 0 |
| 109 | 0 | −0.6 | −0.4 | 0 | 0.6 | 0 | 0 | 0.4 | 0 | 0 | 0 | 0 | 0 | 0 | 0 | 0 |
| 110 | 0 | −0.55 | −0.45 | 0 | 0.55 | 0 | 0 | 0.45 | 0 | 0 | 0 | 0 | 0 | 0 | 0 | 0 |
| 111 | 0 | −0.5 | −0.5 | 0 | 0.5 | 0 | 0 | 0.5 | 0 | 0 | 0 | 0 | 0 | 0 | 0 | 0 |
| 112 | 0 | −0.45 | −0.55 | 0 | 0.45 | 0 | 0 | 0.55 | 0 | 0 | 0 | 0 | 0 | 0 | 0 | 0 |
| 113 | 0 | −0.4 | −0.6 | 0 | 0.4 | 0 | 0 | 0.6 | 0 | 0 | 0 | 0 | 0 | 0 | 0 | 0 |
| 114 | 0 | −0.35 | −0.65 | 0 | 0.35 | 0 | 0 | 0.65 | 0 | 0 | 0 | 0 | 0 | 0 | 0 | 0 |
| 115 | 0 | −0.3 | −0.7 | 0 | 0.3 | 0 | 0 | 0.7 | 0 | 0 | 0 | 0 | 0 | 0 | 0 | 0 |
| 116 | 0 | −0.25 | −0.75 | 0 | 0.25 | 0 | 0 | 0.75 | 0 | 0 | 0 | 0 | 0 | 0 | 0 | 0 |
| 117 | 0 | −0.2 | −0.8 | 0 | 0.2 | 0 | 0 | 0.8 | 0 | 0 | 0 | 0 | 0 | 0 | 0 | 0 |
| 118 | 0 | −0.15 | −0.85 | 0 | 0.15 | 0 | 0 | 0.85 | 0 | 0 | 0 | 0 | 0 | 0 | 0 | 0 |
| 119 | 0 | −0.1 | −0.9 | 0 | 0.1 | 0 | 0 | 0.9 | 0 | 0 | 0 | 0 | 0 | 0 | 0 | 0 |
| 120 | 0 | −0.05 | −0.95 | 0 | 0.05 | 0 | 0 | 0.95 | 0 | 0 | 0 | 0 | 0 | 0 | 0 | 0 |
| 121 | 0 | 0 | −1 | 0 | 0 | 0 | 0 | 1 | 0 | 0 | 0 | 0 | 0 | 0 | 0 | 0 |
| 122 | 0.5 | 0 | −1 | 0 | 0 | 0 | 0 | 0.95 | 0 | 0 | 0 | 0 | 0 | 0 | 0 | 0 |
| 123 | 0.1 | 0 | −1 | 0 | 0 | 0 | 0 | 0.8 | 0 | 0 | 0 | 0 | 0 | 0 | 0 | 0 |
| 124 | 0.15 | 0 | −1 | 0 | 0 | 0 | 0 | 0.85 | 0 | 0 | 0 | 0 | 0 | 0 | 0 | 0 |
| 125 | 0.2 | 0 | −1 | 0 | 0 | 0 | 0 | 0.8 | 0 | 0 | 0 | 0 | 0 | 0 | 0 | 0 |
| 126 | 0.25 | 0 | −1 | 0 | 0 | 0 | 0 | 0.75 | 0 | 0 | 0 | 0 | 0 | 0 | 0 | 0 |
| 127 | 0.3 | 0 | −1 | 0 | 0 | 0 | 0 | 0.7 | 0 | 0 | 0 | 0 | 0 | 0 | 0 | 0 |
| 128 | 0.35 | 0 | −1 | 0 | 0 | 0 | 0 | 0.65 | 0 | 0 | 0 | 0 | 0 | 0 | 0 | 0 |
| 129 | 0.4 | 0 | −1 | 0 | 0 | 0 | 0 | 0.6 | 0 | 0 | 0 | 0 | 0 | 0 | 0 | 0 |
| 130 | 0.45 | 0 | −1 | 0 | 0 | 0 | 0 | 0.55 | 0 | 0 | 0 | 0 | 0 | 0 | 0 | 0 |
| 131 | 0.5 | 0 | −1 | 0 | 0 | 0 | 0 | 0.5 | 0 | 0 | 0 | 0 | 0 | 0 | 0 | 0 |
| 132 | 0.55 | 0 | −1 | 0 | 0 | 0 | 0 | 0.45 | 0 | 0 | 0 | 0 | 0 | 0 | 0 | 0 |
| 133 | 0.6 | 0 | −1 | 0 | 0 | 0 | 0 | 0.4 | 0 | 0 | 0 | 0 | 0 | 0 | 0 | 0 |
| 134 | 0.65 | 0 | −1 | 0 | 0 | 0 | 0 | 0.35 | 0 | 0 | 0 | 0 | 0 | 0 | 0 | 0 |
| 135 | 0.7 | 0 | −1 | 0 | 0 | 0 | 0 | 0.3 | 0 | 0 | 0 | 0 | 0 | 0 | 0 | 0 |
| 136 | 0.75 | 0 | −1 | 0 | 0 | 0 | 0 | 0.25 | 0 | 0 | 0 | 0 | 0 | 0 | 0 | 0 |
| 137 | 0.8 | 0 | −1 | 0 | 0 | 0 | 0 | 0.2 | 0 | 0 | 0 | 0 | 0 | 0 | 0 | 0 |
| 138 | 0.85 | 0 | −1 | 0 | 0 | 0 | 0 | 0.15 | 0 | 0 | 0 | 0 | 0 | 0 | 0 | 0 |
| 139 | 0.9 | 0 | −1 | 0 | 0 | 0 | 0 | 0.1 | 0 | 0 | 0 | 0 | 0 | 0 | 0 | 0 |
| 140 | 0.95 | 0 | −1 | 0 | 0 | 0 | 0 | 0.05 | 0 | 0 | 0 | 0 | 0 | 0 | 0 | 0 |
| 141 | 1 | 0 | −1 | 0 | 0 | 0 | 0 | 0 | 0 | 0 | 0 | 0 | 0 | 0 | 0 | 0 |
| 142 | 0.95 | 0 | −1 | 0 | 0.05 | 0 | 0 | 0 | 0 | 0 | 0 | 0 | 0 | 0 | 0 | 0 |
| 143 | 0.9 | 0 | −1 | 0 | 0.1 | 0 | 0 | 0 | 0 | 0 | 0 | 0 | 0 | 0 | 0 | 0 |
| 144 | 0.85 | 0 | −1 | 0 | 0.15 | 0 | 0 | 0 | 0 | 0 | 0 | 0 | 0 | 0 | 0 | 0 |
| 145 | 0.8 | 0 | −1 | 0 | 0.2 | 0 | 0 | 0 | 0 | 0 | 0 | 0 | 0 | 0 | 0 | 0 |
| 146 | 0.75 | 0 | −1 | 0 | 0.25 | 0 | 0 | 0 | 0 | 0 | 0 | 0 | 0 | 0 | 0 | 0 |
| 147 | 0.7 | 0 | −1 | 0 | 0.3 | 0 | 0 | 0 | 0 | 0 | 0 | 0 | 0 | 0 | 0 | 0 |
| 148 | 0.65 | 0 | −1 | 0 | 0.35 | 0 | 0 | 0 | 0 | 0 | 0 | 0 | 0 | 0 | 0 | 0 |
| 149 | 0.6 | 0 | −1 | 0 | 0.4 | 0 | 0 | 0 | 0 | 0 | 0 | 0 | 0 | 0 | 0 | 0 |
| 150 | 0.55 | 0 | −1 | 0 | 0.45 | 0 | 0 | 0 | 0 | 0 | 0 | 0 | 0 | 0 | 0 | 0 |
| 151 | 0.5 | 0 | −1 | 0 | 0.5 | 0 | 0 | 0 | 0 | 0 | 0 | 0 | 0 | 0 | 0 | 0 |
| 152 | 0.45 | 0 | −1 | 0 | 0.55 | 0 | 0 | 0 | 0 | 0 | 0 | 0 | 0 | 0 | 0 | 0 |
| 153 | 0.4 | 0 | −1 | 0 | 0.6 | 0 | 0 | 0 | 0 | 0 | 0 | 0 | 0 | 0 | 0 | 0 |
| 154 | 0.35 | 0 | −1 | 0 | 0.65 | 0 | 0 | 0 | 0 | 0 | 0 | 0 | 0 | 0 | 0 | 0 |
| 155 | 0.3 | 0 | −1 | 0 | 0.7 | 0 | 0 | 0 | 0 | 0 | 0 | 0 | 0 | 0 | 0 | 0 |
| 156 | 0.25 | 0 | −1 | 0 | 0.75 | 0 | 0 | 0 | 0 | 0 | 0 | 0 | 0 | 0 | 0 | 0 |
| 157 | 0.2 | 0 | −1 | 0 | 0.8 | 0 | 0 | 0 | 0 | 0 | 0 | 0 | 0 | 0 | 0 | 0 |
| 158 | 0.15 | 0 | −1 | 0 | 0.85 | 0 | 0 | 0 | 0 | 0 | 0 | 0 | 0 | 0 | 0 | 0 |
| 159 | 0.1 | 0 | −1 | 0 | 0.9 | 0 | 0 | 0 | 0 | 0 | 0 | 0 | 0 | 0 | 0 | 0 |
| 160 | 0.05 | 0 | −1 | 0 | 0.95 | 0 | 0 | 0 | 0 | 0 | 0 | 0 | 0 | 0 | 0 | 0 |
| 161 | 0 | 0 | −1 | 0 | 1 | 0 | 0 | 0 | 0 | 0 | 0 | 0 | 0 | 0 | 0 | 0 |
| 162 | 0 | 0 | −1 | 0 | 0.95 | 0.05 | 0 | 0 | 0 | 0 | 0 | 0 | 0 | 0 | 0 | 0 |
| 163 | 0 | 0 | −1 | 0 | 0.9 | 0.1 | 0 | 0 | 0 | 0 | 0 | 0 | 0 | 0 | 0 | 0 |
| 164 | 0 | 0 | −1 | 0 | 0.85 | 0.15 | 0 | 0 | 0 | 0 | 0 | 0 | 0 | 0 | 0 | 0 |
| 165 | 0 | −1 | 0 | 0 | 0.8 | 0.2 | 0 | 0 | 0 | 0 | 0 | 0 | 0 | 0 | 0 | 0 |
| 166 | 0 | −1 | 0 | 0 | 0.75 | 0.25 | 0 | 0 | 0 | 0 | 0 | 0 | 0 | 0 | 0 | 0 |
| 167 | 0 | −1 | 0 | 0 | 0.7 | 0.3 | 0 | 0 | 0 | 0 | 0 | 0 | 0 | 0 | 0 | 0 |
| 168 | 0 | −1 | 0 | 0 | 0.65 | 0.35 | 0 | 0 | 0 | 0 | 0 | 0 | 0 | 0 | 0 | 0 |
| 169 | 0 | −1 | 0 | 0 | 0.6 | 0.4 | 0 | 0 | 0 | 0 | 0 | 0 | 0 | 0 | 0 | 0 |
| 170 | 0 | −1 | 0 | 0 | 0.55 | 0.45 | 0 | 0 | 0 | 0 | 0 | 0 | 0 | 0 | 0 | 0 |
| 171 | 0 | −1 | 0 | 0 | 0.5 | 0.5 | 0 | 0 | 0 | 0 | 0 | 0 | 0 | 0 | 0 | 0 |
| 172 | 0 | −1 | 0 | 0 | 0.45 | 0.55 | 0 | 0 | 0 | 0 | 0 | 0 | 0 | 0 | 0 | 0 |
| 173 | 0 | −1 | 0 | 0 | 0.4 | 0.6 | 0 | 0 | 0 | 0 | 0 | 0 | 0 | 0 | 0 | 0 |
| 174 | 0 | −1 | 0 | 0 | 0.35 | 0.65 | 0 | 0 | 0 | 0 | 0 | 0 | 0 | 0 | 0 | 0 |
| 175 | 0 | −1 | 0 | 0 | 0.3 | 0.7 | 0 | 0 | 0 | 0 | 0 | 0 | 0 | 0 | 0 | 0 |
| 176 | 0 | −1 | 0 | 0 | 0.25 | 0.75 | 0 | 0 | 0 | 0 | 0 | 0 | 0 | 0 | 0 | 0 |
| 177 | 0 | −1 | 0 | 0 | 0.2 | 0.8 | 0 | 0 | 0 | 0 | 0 | 0 | 0 | 0 | 0 | 0 |
| 178 | 0 | −1 | 0 | 0 | 0.15 | 0.85 | 0 | 0 | 0 | 0 | 0 | 0 | 0 | 0 | 0 | 0 |

APPENDIX A-continued

Simplified Steering Table

| | Electrode# | | | | | | | | | | | | | | | |
|---|---|---|---|---|---|---|---|---|---|---|---|---|---|---|---|---|
| Stim# | 1 | 2 | 3 | 4 | 5 | 6 | 7 | 8 | 9 | 10 | 11 | 12 | 13 | 14 | 15 | 16 |
| 179 | 0 | −1 | 0 | 0 | 0.1 | 0.9 | 0 | 0 | 0 | 0 | 0 | 0 | 0 | 0 | 0 | 0 |
| 180 | 0 | −1 | 0 | 0 | 0.05 | 0.95 | 0 | 0 | 0 | 0 | 0 | 0 | 0 | 0 | 0 | 0 |
| 181 | 0 | −1 | 0 | 0 | 0 | 1 | 0 | 0 | 0 | 0 | 0 | 0 | 0 | 0 | 0 | 0 |
| 182 | 0.05 | 0 | −0.95 | 0 | −0.05 | 0.95 | 0 | 0 | 0 | 0 | 0 | 0 | 0 | 0 | 0 | 0 |
| 183 | 0.1 | 0 | −0.9 | 0 | −0.1 | 0.9 | 0 | 0 | 0 | 0 | 0 | 0 | 0 | 0 | 0 | 0 |
| 184 | 0.15 | 0 | −0.85 | 0 | −0.15 | 0.85 | 0 | 0 | 0 | 0 | 0 | 0 | 0 | 0 | 0 | 0 |
| 185 | 0.2 | 0 | −0.8 | 0 | −0.2 | 0.8 | 0 | 0 | 0 | 0 | 0 | 0 | 0 | 0 | 0 | 0 |
| 186 | 0.25 | 0 | −0.75 | 0 | −0.25 | 0.75 | 0 | 0 | 0 | 0 | 0 | 0 | 0 | 0 | 0 | 0 |
| 187 | 0.3 | 0 | −0.7 | 0 | −0.3 | 0.7 | 0 | 0 | 0 | 0 | 0 | 0 | 0 | 0 | 0 | 0 |
| 188 | 0.35 | 0 | −0.65 | 0 | −0.35 | 0.65 | 0 | 0 | 0 | 0 | 0 | 0 | 0 | 0 | 0 | 0 |
| 189 | 0.4 | 0 | −0.6 | 0 | −0.4 | 0.6 | 0 | 0 | 0 | 0 | 0 | 0 | 0 | 0 | 0 | 0 |
| 190 | 0.45 | 0 | −0.55 | 0 | −0.45 | 0.55 | 0 | 0 | 0 | 0 | 0 | 0 | 0 | 0 | 0 | 0 |
| 191 | 0.5 | 0 | −0.5 | 0 | −0.5 | 0.5 | 0 | 0 | 0 | 0 | 0 | 0 | 0 | 0 | 0 | 0 |
| 192 | 0.55 | 0 | −0.45 | 0 | −0.55 | 0.45 | 0 | 0 | 0 | 0 | 0 | 0 | 0 | 0 | 0 | 0 |
| 193 | 0.6 | 0 | −0.4 | 0 | −0.6 | 0.4 | 0 | 0 | 0 | 0 | 0 | 0 | 0 | 0 | 0 | 0 |
| 194 | 0.65 | 0 | −0.35 | 0 | −0.65 | 0.35 | 0 | 0 | 0 | 0 | 0 | 0 | 0 | 0 | 0 | 0 |
| 195 | 0.7 | 0 | −0.3 | 0 | −0.7 | 0.3 | 0 | 0 | 0 | 0 | 0 | 0 | 0 | 0 | 0 | 0 |
| 196 | 0.75 | 0 | −0.25 | 0 | −0.75 | 0.25 | 0 | 0 | 0 | 0 | 0 | 0 | 0 | 0 | 0 | 0 |
| 197 | 0.8 | 0 | −0.2 | 0 | −0.8 | 0.2 | 0 | 0 | 0 | 0 | 0 | 0 | 0 | 0 | 0 | 0 |
| 198 | 0.85 | 0 | −0.15 | 0 | −0.85 | 0.15 | 0 | 0 | 0 | 0 | 0 | 0 | 0 | 0 | 0 | 0 |
| 199 | 0.9 | 0 | −0.1 | 0 | −0.9 | 0.1 | 0 | 0 | 0 | 0 | 0 | 0 | 0 | 0 | 0 | 0 |
| 200 | 0.95 | 0 | −0.05 | 0 | −0.95 | 0.05 | 0 | 0 | 0 | 0 | 0 | 0 | 0 | 0 | 0 | 0 |
| 201 | 1 | 0 | 0 | 0 | −1 | 0 | 0 | 0 | 0 | 0 | 0 | 0 | 0 | 0 | 0 | 0 |
| 202 | 0.95 | 0.05 | 0 | 0 | −1 | 0 | 0 | 0 | 0 | 0 | 0 | 0 | 0 | 0 | 0 | 0 |
| 203 | 0.9 | 0.1 | 0 | 0 | −1 | 0 | 0 | 0 | 0 | 0 | 0 | 0 | 0 | 0 | 0 | 0 |
| 204 | 0.85 | 0.15 | 0 | 0 | −1 | 0 | 0 | 0 | 0 | 0 | 0 | 0 | 0 | 0 | 0 | 0 |
| 205 | 0.8 | 0.2 | 0 | 0 | −1 | 0 | 0 | 0 | 0 | 0 | 0 | 0 | 0 | 0 | 0 | 0 |
| 206 | 0.75 | 0.25 | 0 | −1 | 0 | 0 | 0 | 0 | 0 | 0 | 0 | 0 | 0 | 0 | 0 | 0 |
| 207 | 0.7 | 0.3 | 0 | −1 | 0 | 0 | 0 | 0 | 0 | 0 | 0 | 0 | 0 | 0 | 0 | 0 |
| 208 | 0.65 | 0.35 | 0 | −1 | 0 | 0 | 0 | 0 | 0 | 0 | 0 | 0 | 0 | 0 | 0 | 0 |
| 209 | 0.6 | 0.4 | 0 | −1 | 0 | 0 | 0 | 0 | 0 | 0 | 0 | 0 | 0 | 0 | 0 | 0 |
| 210 | 0.55 | 0.45 | 0 | −1 | 0 | 0 | 0 | 0 | 0 | 0 | 0 | 0 | 0 | 0 | 0 | 0 |
| 211 | 0.5 | 0.5 | 0 | −1 | 0 | 0 | 0 | 0 | 0 | 0 | 0 | 0 | 0 | 0 | 0 | 0 |
| 212 | 0.45 | 0.55 | 0 | −1 | 0 | 0 | 0 | 0 | 0 | 0 | 0 | 0 | 0 | 0 | 0 | 0 |
| 213 | 0.4 | 0.6 | 0 | −1 | 0 | 0 | 0 | 0 | 0 | 0 | 0 | 0 | 0 | 0 | 0 | 0 |
| 214 | 0.35 | 0.65 | 0 | −1 | 0 | 0 | 0 | 0 | 0 | 0 | 0 | 0 | 0 | 0 | 0 | 0 |
| 215 | 0.3 | 0.7 | 0 | −1 | 0 | 0 | 0 | 0 | 0 | 0 | 0 | 0 | 0 | 0 | 0 | 0 |
| 216 | 0.25 | 0.75 | 0 | −1 | 0 | 0 | 0 | 0 | 0 | 0 | 0 | 0 | 0 | 0 | 0 | 0 |
| 217 | 0.2 | 0.8 | 0 | −1 | 0 | 0 | 0 | 0 | 0 | 0 | 0 | 0 | 0 | 0 | 0 | 0 |
| 218 | 0.15 | 0.85 | 0 | −1 | 0 | 0 | 0 | 0 | 0 | 0 | 0 | 0 | 0 | 0 | 0 | 0 |
| 219 | 0.1 | 0.9 | 0 | −1 | 0 | 0 | 0 | 0 | 0 | 0 | 0 | 0 | 0 | 0 | 0 | 0 |
| 220 | 0.05 | 0.95 | 0 | −1 | 0 | 0 | 0 | 0 | 0 | 0 | 0 | 0 | 0 | 0 | 0 | 0 |
| 221 | 0 | 1 | 0 | −1 | 0 | 0 | 0 | 0 | 0 | 0 | 0 | 0 | 0 | 0 | 0 | 0 |
| 222 | 0 | 0.95 | 0 | −1 | 0 | 0.05 | 0 | 0 | 0 | 0 | 0 | 0 | 0 | 0 | 0 | 0 |
| 223 | 0 | 0.9 | 0 | −1 | 0 | 0.1 | 0 | 0 | 0 | 0 | 0 | 0 | 0 | 0 | 0 | 0 |
| 224 | 0 | 0.85 | 0 | −1 | 0 | 0.15 | 0 | 0 | 0 | 0 | 0 | 0 | 0 | 0 | 0 | 0 |
| 225 | 0 | 0.8 | 0 | −1 | 0 | 0.2 | 0 | 0 | 0 | 0 | 0 | 0 | 0 | 0 | 0 | 0 |
| 226 | 0 | 0.75 | 0 | −1 | 0 | 0.25 | 0 | 0 | 0 | 0 | 0 | 0 | 0 | 0 | 0 | 0 |
| 227 | 0 | 0.7 | 0 | −1 | 0 | 0.3 | 0 | 0 | 0 | 0 | 0 | 0 | 0 | 0 | 0 | 0 |
| 228 | 0 | 0.65 | 0 | −1 | 0 | 0.35 | 0 | 0 | 0 | 0 | 0 | 0 | 0 | 0 | 0 | 0 |
| 229 | 0 | 0.6 | 0 | −1 | 0 | 0.4 | 0 | 0 | 0 | 0 | 0 | 0 | 0 | 0 | 0 | 0 |
| 230 | 0 | 0.55 | 0 | −1 | 0 | 0.45 | 0 | 0 | 0 | 0 | 0 | 0 | 0 | 0 | 0 | 0 |
| 231 | 0 | 0.5 | 0 | −1 | 0 | 0.5 | 0 | 0 | 0 | 0 | 0 | 0 | 0 | 0 | 0 | 0 |
| 232 | 0 | 0.45 | 0 | −1 | 0 | 0.55 | 0 | 0 | 0 | 0 | 0 | 0 | 0 | 0 | 0 | 0 |
| 233 | 0 | 0.4 | 0 | −1 | 0 | 0.6 | 0 | 0 | 0 | 0 | 0 | 0 | 0 | 0 | 0 | 0 |
| 234 | 0 | 0.35 | 0 | −1 | 0 | 0.65 | 0 | 0 | 0 | 0 | 0 | 0 | 0 | 0 | 0 | 0 |
| 235 | 0 | 0.3 | 0 | −1 | 0 | 0.7 | 0 | 0 | 0 | 0 | 0 | 0 | 0 | 0 | 0 | 0 |
| 236 | 0 | 0.25 | 0 | −1 | 0 | 0.75 | 0 | 0 | 0 | 0 | 0 | 0 | 0 | 0 | 0 | 0 |
| 237 | 0 | 0.2 | 0 | −1 | 0 | 0.8 | 0 | 0 | 0 | 0 | 0 | 0 | 0 | 0 | 0 | 0 |
| 238 | 0 | 0.15 | 0 | −1 | 0 | 0.85 | 0 | 0 | 0 | 0 | 0 | 0 | 0 | 0 | 0 | 0 |
| 239 | 0 | 0.1 | 0 | −1 | 0 | 0.9 | 0 | 0 | 0 | 0 | 0 | 0 | 0 | 0 | 0 | 0 |
| 240 | 0 | 0.05 | 0 | −1 | 0 | 0.95 | 0 | 0 | 0 | 0 | 0 | 0 | 0 | 0 | 0 | 0 |
| 241 | 0 | 0 | 0 | −1 | 0 | 1 | 0 | 0 | 0 | 0 | 0 | 0 | 0 | 0 | 0 | 0 |
| 242 | 0 | 0 | 0 | −1 | 0 | 0.95 | 0.05 | 0 | 0 | 0 | 0 | 0 | 0 | 0 | 0 | 0 |
| 243 | 0 | 0 | 0 | −1 | 0 | 0.9 | 0.1 | 0 | 0 | 0 | 0 | 0 | 0 | 0 | 0 | 0 |
| 244 | 0 | 0 | 0 | −1 | 0 | 0.85 | 0.15 | 0 | 0 | 0 | 0 | 0 | 0 | 0 | 0 | 0 |
| 245 | 0 | 0 | 0 | −1 | 0 | 0.8 | 0.2 | 0 | 0 | 0 | 0 | 0 | 0 | 0 | 0 | 0 |
| 246 | 0 | 0 | 0 | −1 | 0 | 0.75 | 0.25 | 0 | 0 | 0 | 0 | 0 | 0 | 0 | 0 | 0 |
| 247 | 0 | 0 | 0 | −1 | 0 | 0.7 | 0.3 | 0 | 0 | 0 | 0 | 0 | 0 | 0 | 0 | 0 |
| 248 | 0 | 0 | 0 | −1 | 0 | 0.65 | 0.35 | 0 | 0 | 0 | 0 | 0 | 0 | 0 | 0 | 0 |
| 249 | 0 | 0 | 0 | −1 | 0 | 0.6 | 0.4 | 0 | 0 | 0 | 0 | 0 | 0 | 0 | 0 | 0 |
| 250 | 0 | 0 | 0 | −1 | 0 | 0.55 | 0.45 | 0 | 0 | 0 | 0 | 0 | 0 | 0 | 0 | 0 |
| 251 | 0 | 0 | 0 | −1 | 0 | 0.5 | 0.5 | 0 | 0 | 0 | 0 | 0 | 0 | 0 | 0 | 0 |
| 252 | 0 | 0 | 0 | −1 | 0 | 0.45 | 0.55 | 0 | 0 | 0 | 0 | 0 | 0 | 0 | 0 | 0 |

APPENDIX A-continued

Simplified Steering Table

| Stim# | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 253 | 0 | 0 | 0 | −1 | 0 | 0.4 | 0.6 | 0 | 0 | 0 | 0 | 0 | 0 | 0 | 0 | 0 |
| 254 | 0 | 0 | 0 | −1 | 0 | 0.35 | 0.65 | 0 | 0 | 0 | 0 | 0 | 0 | 0 | 0 | 0 |
| 256 | 0 | 0 | 0 | −1 | 0 | 0.3 | 0.7 | 0 | 0 | 0 | 0 | 0 | 0 | 0 | 0 | 0 |
| 257 | 0 | 0 | 0 | −1 | 0 | 0.25 | 0.75 | 0 | 0 | 0 | 0 | 0 | 0 | 0 | 0 | 0 |
| 258 | 0 | 0 | 0 | −1 | 0 | 0.2 | 0.8 | 0 | 0 | 0 | 0 | 0 | 0 | 0 | 0 | 0 |
| 259 | 0 | 0 | 0 | −1 | 0 | 0.15 | 0.85 | 0 | 0 | 0 | 0 | 0 | 0 | 0 | 0 | 0 |
| 260 | 0 | 0 | 0 | −1 | 0 | 0.1 | 0.9 | 0 | 0 | 0 | 0 | 0 | 0 | 0 | 0 | 0 |
| 261 | 0 | 0 | 0 | −1 | 0 | 0.05 | 0.95 | 0 | 0 | 0 | 0 | 0 | 0 | 0 | 0 | 0 |
| 262 | 0 | 0.05 | 0 | −0.95 | −0.05 | 0 | 1 | 0 | 0 | 0 | 0 | 0 | 0 | 0 | 0 | 0 |
| 263 | 0 | 0.1 | 0 | −0.9 | −0.1 | 0 | 0.95 | 0 | 0 | 0 | 0 | 0 | 0 | 0 | 0 | 0 |
| 264 | 0 | 0.15 | 0 | −0.85 | −0.15 | 0 | 0.9 | 0 | 0 | 0 | 0 | 0 | 0 | 0 | 0 | 0 |
| 265 | 0 | 0.2 | 0 | −0.8 | −0.2 | 0 | 0.85 | 0 | 0 | 0 | 0 | 0 | 0 | 0 | 0 | 0 |
| 266 | 0 | 0.25 | 0 | −0.75 | −0.25 | 0 | 0.8 | 0 | 0 | 0 | 0 | 0 | 0 | 0 | 0 | 0 |
| 267 | 0 | 0.3 | 0 | −0.7 | −0.3 | 0 | 0.75 | 0 | 0 | 0 | 0 | 0 | 0 | 0 | 0 | 0 |
| 268 | 0 | 0.35 | 0 | −0.65 | −0.35 | 0 | 0.7 | 0 | 0 | 0 | 0 | 0 | 0 | 0 | 0 | 0 |
| 269 | 0 | 0.4 | 0 | −0.6 | −0.4 | 0 | 0.65 | 0 | 0 | 0 | 0 | 0 | 0 | 0 | 0 | 0 |
| 270 | 0 | 0.45 | 0 | −0.55 | −0.45 | 0 | 0.6 | 0 | 0 | 0 | 0 | 0 | 0 | 0 | 0 | 0 |
| 271 | 0 | 0.5 | 0 | −0.5 | −0.5 | 0 | 0.55 | 0 | 0 | 0 | 0 | 0 | 0 | 0 | 0 | 0 |
| 272 | 0 | 0.55 | 0 | −0.45 | −0.55 | 0 | 0.5 | 0 | 0 | 0 | 0 | 0 | 0 | 0 | 0 | 0 |
| 273 | 0 | 0.6 | 0 | −0.4 | −0.6 | 0 | 0.45 | 0 | 0 | 0 | 0 | 0 | 0 | 0 | 0 | 0 |
| 274 | 0 | 0.65 | 0 | −0.35 | −0.65 | 0 | 0.4 | 0 | 0 | 0 | 0 | 0 | 0 | 0 | 0 | 0 |
| 275 | 0 | 0.7 | 0 | −0.3 | −0.7 | 0 | 0.35 | 0 | 0 | 0 | 0 | 0 | 0 | 0 | 0 | 0 |
| 276 | 0 | 0.75 | 0 | −0.25 | −0.75 | 0 | 0.3 | 0 | 0 | 0 | 0 | 0 | 0 | 0 | 0 | 0 |
| 277 | 0 | 0.8 | 0 | −0.2 | −0.8 | 0 | 0.25 | 0 | 0 | 0 | 0 | 0 | 0 | 0 | 0 | 0 |
| 278 | 0 | 0.85 | 0 | −0.15 | −0.85 | 0 | 0.2 | 0 | 0 | 0 | 0 | 0 | 0 | 0 | 0 | 0 |
| 279 | 0 | 0.9 | 0 | −0.1 | −0.9 | 0 | 0.15 | 0 | 0 | 0 | 0 | 0 | 0 | 0 | 0 | 0 |
| 280 | 0 | 0.95 | 0 | −0.05 | −0.95 | 0 | 0.1 | 0 | 0 | 0 | 0 | 0 | 0 | 0 | 0 | 0 |
| 281 | 0 | 1 | 0 | 0 | −1 | 0 | 0.05 | 0 | 0 | 0 | 0 | 0 | 0 | 0 | 0 | 0 |
| 282 | 0 | 0.95 | 0.05 | 0 | −1 | 0 | 0 | 0 | 0 | 0 | 0 | 0 | 0 | 0 | 0 | 0 |
| 283 | 0 | 0.9 | 0.1 | 0 | −1 | 0 | 0 | 0 | 0 | 0 | 0 | 0 | 0 | 0 | 0 | 0 |
| 284 | 0 | 0.85 | 0.15 | 0 | −1 | 0 | 0 | 0 | 0 | 0 | 0 | 0 | 0 | 0 | 0 | 0 |
| 285 | 0 | 0.8 | 0.2 | 0 | −1 | 0 | 0 | 0 | 0 | 0 | 0 | 0 | 0 | 0 | 0 | 0 |
| 286 | 0 | 0.75 | 0.25 | 0 | −1 | 0 | 0 | 0 | 0 | 0 | 0 | 0 | 0 | 0 | 0 | 0 |
| 287 | 0 | 0.7 | 0.3 | 0 | −1 | 0 | 0 | 0 | 0 | 0 | 0 | 0 | 0 | 0 | 0 | 0 |
| 288 | 0 | 0.65 | 0.35 | 0 | −1 | 0 | 0 | 0 | 0 | 0 | 0 | 0 | 0 | 0 | 0 | 0 |
| 289 | 0 | 0.6 | 0.4 | 0 | −1 | 0 | 0 | 0 | 0 | 0 | 0 | 0 | 0 | 0 | 0 | 0 |
| 290 | 0 | 0.55 | 0.45 | 0 | −1 | 0 | 0 | 0 | 0 | 0 | 0 | 0 | 0 | 0 | 0 | 0 |
| 291 | 0 | 0.5 | 0.5 | 0 | −1 | 0 | 0 | 0 | 0 | 0 | 0 | 0 | 0 | 0 | 0 | 0 |
| 292 | 0 | 0.45 | 0.55 | 0 | −1 | 0 | 0 | 0 | 0 | 0 | 0 | 0 | 0 | 0 | 0 | 0 |
| 293 | 0 | 0.4 | 0.6 | 0 | −1 | 0 | 0 | 0 | 0 | 0 | 0 | 0 | 0 | 0 | 0 | 0 |
| 294 | 0 | 0.35 | 0.65 | 0 | −1 | 0 | 0 | 0 | 0 | 0 | 0 | 0 | 0 | 0 | 0 | 0 |
| 295 | 0 | 0.3 | 0.7 | 0 | −1 | 0 | 0 | 0 | 0 | 0 | 0 | 0 | 0 | 0 | 0 | 0 |
| 296 | 0 | 0.25 | 0.75 | 0 | −1 | 0 | 0 | 0 | 0 | 0 | 0 | 0 | 0 | 0 | 0 | 0 |
| 297 | 0 | 0.2 | 0.8 | 0 | −1 | 0 | 0 | 0 | 0 | 0 | 0 | 0 | 0 | 0 | 0 | 0 |
| 298 | 0 | 0.15 | 0.85 | 0 | −1 | 0 | 0 | 0 | 0 | 0 | 0 | 0 | 0 | 0 | 0 | 0 |
| 299 | 0 | 0.1 | 0.9 | 0 | −1 | 0 | 0 | 0 | 0 | 0 | 0 | 0 | 0 | 0 | 0 | 0 |
| 300 | 0 | 0.05 | 0.95 | 0 | −1 | 0 | 0 | 0 | 0 | 0 | 0 | 0 | 0 | 0 | 0 | 0 |
| 301 | 0 | 0 | 1 | 0 | −1 | 0 | 0 | 0 | 0 | 0 | 0 | 0 | 0 | 0 | 0 | 0 |
| 302 | 0 | 0 | 0.95 | 0 | −1 | 0 | 0.05 | 0 | 0 | 0 | 0 | 0 | 0 | 0 | 0 | 0 |
| 303 | 0 | 0 | 0.9 | 0 | −1 | 0 | 0.1 | 0 | 0 | 0 | 0 | 0 | 0 | 0 | 0 | 0 |
| 304 | 0 | 0 | 0.85 | 0 | −1 | 0 | 0.15 | 0 | 0 | 0 | 0 | 0 | 0 | 0 | 0 | 0 |
| 305 | 0 | 0 | 0.8 | 0 | −1 | 0 | 0.2 | 0 | 0 | 0 | 0 | 0 | 0 | 0 | 0 | 0 |
| 306 | 0 | 0 | 0.75 | 0 | −1 | 0 | 0.25 | 0 | 0 | 0 | 0 | 0 | 0 | 0 | 0 | 0 |
| 307 | 0 | 0 | 0.7 | 0 | −1 | 0 | 0.3 | 0 | 0 | 0 | 0 | 0 | 0 | 0 | 0 | 0 |
| 308 | 0 | 0 | 0.65 | 0 | −1 | 0 | 0.35 | 0 | 0 | 0 | 0 | 0 | 0 | 0 | 0 | 0 |
| 309 | 0 | 0 | 0.6 | 0 | −1 | 0 | 0.4 | 0 | 0 | 0 | 0 | 0 | 0 | 0 | 0 | 0 |
| 310 | 0 | 0 | 0.55 | 0 | −1 | 0 | 0.45 | 0 | 0 | 0 | 0 | 0 | 0 | 0 | 0 | 0 |
| 311 | 0 | 0 | 0.5 | 0 | −1 | 0 | 0.5 | 0 | 0 | 0 | 0 | 0 | 0 | 0 | 0 | 0 |
| 312 | 0 | 0 | 0.45 | 0 | −1 | 0 | 0.55 | 0 | 0 | 0 | 0 | 0 | 0 | 0 | 0 | 0 |
| 313 | 0 | 0 | 0.4 | 0 | −1 | 0 | 0.6 | 0 | 0 | 0 | 0 | 0 | 0 | 0 | 0 | 0 |
| 314 | 0 | 0 | 0.35 | 0 | −1 | 0 | 0.65 | 0 | 0 | 0 | 0 | 0 | 0 | 0 | 0 | 0 |
| 315 | 0 | 0 | 0.3 | 0 | −1 | 0 | 0.7 | 0 | 0 | 0 | 0 | 0 | 0 | 0 | 0 | 0 |
| 316 | 0 | 0 | 0.25 | 0 | −1 | 0 | 0.75 | 0 | 0 | 0 | 0 | 0 | 0 | 0 | 0 | 0 |
| 317 | 0 | 0 | 0.2 | 0 | −1 | 0 | 0.8 | 0 | 0 | 0 | 0 | 0 | 0 | 0 | 0 | 0 |
| 318 | 0 | 0 | 0.15 | 0 | −1 | 0 | 0.85 | 0 | 0 | 0 | 0 | 0 | 0 | 0 | 0 | 0 |
| 319 | 0 | 0 | 0.1 | 0 | −1 | 0 | 0.9 | 0 | 0 | 0 | 0 | 0 | 0 | 0 | 0 | 0 |
| 320 | 0 | 0 | 0.05 | 0 | −1 | 0 | 0.95 | 0 | 0 | 0 | 0 | 0 | 0 | 0 | 0 | 0 |
| 321 | 0 | 0 | 0 | 0 | −1 | 0 | 1 | 0 | 0 | 0 | 0 | 0 | 0 | 0 | 0 | 0 |
| 322 | 0 | 0 | 0 | 0 | −1 | 0 | 0.95 | 0.05 | 0 | 0 | 0 | 0 | 0 | 0 | 0 | 0 |
| 323 | 0 | 0 | 0 | 0 | −1 | 0 | 0.9 | 0.1 | 0 | 0 | 0 | 0 | 0 | 0 | 0 | 0 |
| 324 | 0 | 0 | 0 | 0 | −1 | 0 | 0.85 | 0.15 | 0 | 0 | 0 | 0 | 0 | 0 | 0 | 0 |
| 325 | 0 | 0 | 0 | 0 | −1 | 0 | 0.8 | 0.2 | 0 | 0 | 0 | 0 | 0 | 0 | 0 | 0 |
| 326 | 0 | 0 | 0 | 0 | −1 | 0 | 0.75 | 0.25 | 0 | 0 | 0 | 0 | 0 | 0 | 0 | 0 |
| 327 | 0 | 0 | 0 | 0 | −1 | 0 | 0.7 | 0.3 | 0 | 0 | 0 | 0 | 0 | 0 | 0 | 0 |

APPENDIX A-continued

Simplified Steering Table

| | Electrode# | | | | | | | | | | | | | | | |
|---|---|---|---|---|---|---|---|---|---|---|---|---|---|---|---|---|
| Stim# | 1 | 2 | 3 | 4 | 5 | 6 | 7 | 8 | 9 | 10 | 11 | 12 | 13 | 14 | 15 | 16 |
| 328 | 0 | 0 | 0 | 0 | −1 | 0 | 0.65 | 0.35 | 0 | 0 | 0 | 0 | 0 | 0 | 0 | 0 |
| 329 | 0 | 0 | 0 | 0 | −1 | 0 | 0.6 | 0.4 | 0 | 0 | 0 | 0 | 0 | 0 | 0 | 0 |
| 330 | 0 | 0 | 0 | 0 | −1 | 0 | 0.55 | 0.45 | 0 | 0 | 0 | 0 | 0 | 0 | 0 | 0 |
| 331 | 0 | 0 | 0 | 0 | −1 | 0 | 0.5 | 0.5 | 0 | 0 | 0 | 0 | 0 | 0 | 0 | 0 |
| 332 | 0 | 0 | 0 | 0 | −1 | 0 | 0.45 | 0.55 | 0 | 0 | 0 | 0 | 0 | 0 | 0 | 0 |
| 333 | 0 | 0 | 0 | 0 | −1 | 0 | 0.4 | 0.6 | 0 | 0 | 0 | 0 | 0 | 0 | 0 | 0 |
| 334 | 0 | 0 | 0 | 0 | −1 | 0 | 0.35 | 0.65 | 0 | 0 | 0 | 0 | 0 | 0 | 0 | 0 |
| 335 | 0 | 0 | 0 | 0 | −1 | 0 | 0.3 | 0.7 | 0 | 0 | 0 | 0 | 0 | 0 | 0 | 0 |
| 336 | 0 | 0 | 0 | 0 | −1 | 0 | 0.25 | 0.75 | 0 | 0 | 0 | 0 | 0 | 0 | 0 | 0 |
| 337 | 0 | 0 | 0 | 0 | −1 | 0 | 0.2 | 0.8 | 0 | 0 | 0 | 0 | 0 | 0 | 0 | 0 |
| 338 | 0 | 0 | 0 | 0 | −1 | 0 | 0.15 | 0.85 | 0 | 0 | 0 | 0 | 0 | 0 | 0 | 0 |
| 339 | 0 | 0 | 0 | 0 | −1 | 0 | 0.1 | 0.9 | 0 | 0 | 0 | 0 | 0 | 0 | 0 | 0 |
| 340 | 0 | 0 | 0 | 0 | −1 | 0 | 0.05 | 0.95 | 0 | 0 | 0 | 0 | 0 | 0 | 0 | 0 |
| 341 | 0 | 0 | 0 | 0 | −1 | 0 | 0 | 1 | 0 | 0 | 0 | 0 | 0 | 0 | 0 | 0 |
| 342 | 0 | 0 | 0.05 | 0 | −0.95 | −0.05 | 0 | 0.95 | 0 | 0 | 0 | 0 | 0 | 0 | 0 | 0 |
| 343 | 0 | 0 | 0.1 | 0 | −0.9 | −0.1 | 0 | 0.9 | 0 | 0 | 0 | 0 | 0 | 0 | 0 | 0 |
| 344 | 0 | 0 | 0.15 | 0 | −0.85 | −0.15 | 0 | 0.85 | 0 | 0 | 0 | 0 | 0 | 0 | 0 | 0 |
| 345 | 0 | 0 | 0.2 | 0 | −0.8 | −0.2 | 0 | 0.8 | 0 | 0 | 0 | 0 | 0 | 0 | 0 | 0 |
| 346 | 0 | 0 | 0.25 | 0 | −0.75 | −0.25 | 0 | 0.75 | 0 | 0 | 0 | 0 | 0 | 0 | 0 | 0 |
| 347 | 0 | 0 | 0.3 | 0 | −0.7 | −0.3 | 0 | 0.7 | 0 | 0 | 0 | 0 | 0 | 0 | 0 | 0 |
| 348 | 0 | 0 | 0.35 | 0 | −0.65 | −0.35 | 0 | 0.65 | 0 | 0 | 0 | 0 | 0 | 0 | 0 | 0 |
| 349 | 0 | 0 | 0.4 | 0 | −0.6 | −0.4 | 0 | 0.6 | 0 | 0 | 0 | 0 | 0 | 0 | 0 | 0 |
| 350 | 0 | 0 | 0.45 | 0 | −0.55 | −0.45 | 0 | 0.55 | 0 | 0 | 0 | 0 | 0 | 0 | 0 | 0 |
| 351 | 0 | 0 | 0.5 | 0 | −0.5 | −0.5 | 0 | 0.5 | 0 | 0 | 0 | 0 | 0 | 0 | 0 | 0 |
| 352 | 0 | 0 | 0.55 | 0 | −0.45 | −0.55 | 0 | 0.45 | 0 | 0 | 0 | 0 | 0 | 0 | 0 | 0 |
| 353 | 0 | 0 | 0.6 | 0 | −0.4 | −0.6 | 0 | 0.4 | 0 | 0 | 0 | 0 | 0 | 0 | 0 | 0 |
| 354 | 0 | 0 | 0.65 | 0 | −0.35 | −0.65 | 0 | 0.35 | 0 | 0 | 0 | 0 | 0 | 0 | 0 | 0 |
| 355 | 0 | 0 | 0.7 | 0 | −0.3 | −0.7 | 0 | 0.3 | 0 | 0 | 0 | 0 | 0 | 0 | 0 | 0 |
| 356 | 0 | 0 | 0.75 | 0 | −0.25 | −0.75 | 0 | 0.25 | 0 | 0 | 0 | 0 | 0 | 0 | 0 | 0 |
| 357 | 0 | 0 | 0.8 | 0 | −0.2 | −0.8 | 0 | 0.2 | 0 | 0 | 0 | 0 | 0 | 0 | 0 | 0 |
| 358 | 0 | 0 | 0.85 | 0 | −0.15 | −0.85 | 0 | 0.15 | 0 | 0 | 0 | 0 | 0 | 0 | 0 | 0 |
| 359 | 0 | 0 | 0.9 | 0 | −0.1 | −0.9 | 0 | 0.1 | 0 | 0 | 0 | 0 | 0 | 0 | 0 | 0 |
| 360 | 0 | 0 | 0.95 | 0 | −0.05 | −0.95 | 0 | 0.05 | 0 | 0 | 0 | 0 | 0 | 0 | 0 | 0 |
| 361 | 0 | 0 | 1 | 0 | 0 | −1 | 0 | 0 | 0 | 0 | 0 | 0 | 0 | 0 | 0 | 0 |
| 362 | 0 | 0 | 0.95 | 0.05 | 0 | −1 | 0 | 0 | 0 | 0 | 0 | 0 | 0 | 0 | 0 | 0 |
| 363 | 0 | 0 | 0.9 | 0.1 | 0 | −1 | 0 | 0 | 0 | 0 | 0 | 0 | 0 | 0 | 0 | 0 |
| 364 | 0 | 0 | 0.85 | 0.15 | 0 | −1 | 0 | 0 | 0 | 0 | 0 | 0 | 0 | 0 | 0 | 0 |
| 365 | 0 | 0 | 0.8 | 0.2 | 0 | −1 | 0 | 0 | 0 | 0 | 0 | 0 | 0 | 0 | 0 | 0 |
| 366 | 0 | 0 | 0.75 | 0.25 | 0 | −1 | 0 | 0 | 0 | 0 | 0 | 0 | 0 | 0 | 0 | 0 |
| 367 | 0 | 0 | 0.7 | 0.3 | 0 | −1 | 0 | 0 | 0 | 0 | 0 | 0 | 0 | 0 | 0 | 0 |
| 368 | 0 | 0 | 0.65 | 0.35 | 0 | −1 | 0 | 0 | 0 | 0 | 0 | 0 | 0 | 0 | 0 | 0 |
| 369 | 0 | 0 | 0.6 | 0.4 | 0 | −1 | 0 | 0 | 0 | 0 | 0 | 0 | 0 | 0 | 0 | 0 |
| 370 | 0 | 0 | 0.55 | 0.45 | 0 | −1 | 0 | 0 | 0 | 0 | 0 | 0 | 0 | 0 | 0 | 0 |
| 371 | 0 | 0 | 0.5 | 0.5 | 0 | −1 | 0 | 0 | 0 | 0 | 0 | 0 | 0 | 0 | 0 | 0 |
| 372 | 0 | 0 | 0.45 | 0.55 | 0 | −1 | 0 | 0 | 0 | 0 | 0 | 0 | 0 | 0 | 0 | 0 |
| 373 | 0 | 0 | 0.4 | 0.6 | 0 | −1 | 0 | 0 | 0 | 0 | 0 | 0 | 0 | 0 | 0 | 0 |
| 374 | 0 | 0 | 0.35 | 0.65 | 0 | −1 | 0 | 0 | 0 | 0 | 0 | 0 | 0 | 0 | 0 | 0 |
| 375 | 0 | 0 | 0.3 | 0.7 | 0 | −1 | 0 | 0 | 0 | 0 | 0 | 0 | 0 | 0 | 0 | 0 |
| 376 | 0 | 0 | 0.25 | 0.75 | 0 | −1 | 0 | 0 | 0 | 0 | 0 | 0 | 0 | 0 | 0 | 0 |
| 377 | 0 | 0 | 0.2 | 0.8 | 0 | −1 | 0 | 0 | 0 | 0 | 0 | 0 | 0 | 0 | 0 | 0 |
| 378 | 0 | 0 | 0.15 | 0.85 | 0 | −1 | 0 | 0 | 0 | 0 | 0 | 0 | 0 | 0 | 0 | 0 |
| 379 | 0 | 0 | 0.1 | 0.9 | 0 | −1 | 0 | 0 | 0 | 0 | 0 | 0 | 0 | 0 | 0 | 0 |
| 380 | 0 | 0 | 0.05 | 0.95 | 0 | −1 | 0 | 0 | 0 | 0 | 0 | 0 | 0 | 0 | 0 | 0 |
| 381 | 0 | 0 | 0 | 1 | 0 | −1 | 0 | 0 | 0 | 0 | 0 | 0 | 0 | 0 | 0 | 0 |
| 382 | 0 | 0 | 0 | 0.95 | 0 | −1 | 0 | 0.05 | 0 | 0 | 0 | 0 | 0 | 0 | 0 | 0 |
| 383 | 0 | 0 | 0 | 0.9 | 0 | −1 | 0 | 0.1 | 0 | 0 | 0 | 0 | 0 | 0 | 0 | 0 |
| 384 | 0 | 0 | 0 | 0.85 | 0 | −1 | 0 | 0.15 | 0 | 0 | 0 | 0 | 0 | 0 | 0 | 0 |
| 385 | 0 | 0 | 0 | 0.8 | 0 | −1 | 0 | 0.2 | 0 | 0 | 0 | 0 | 0 | 0 | 0 | 0 |
| 386 | 0 | 0 | 0 | 0.75 | 0 | −1 | 0 | 0.25 | 0 | 0 | 0 | 0 | 0 | 0 | 0 | 0 |
| 387 | 0 | 0 | 0 | 0.7 | 0 | −1 | 0 | 0.3 | 0 | 0 | 0 | 0 | 0 | 0 | 0 | 0 |
| 388 | 0 | 0 | 0 | 0.65 | 0 | −1 | 0 | 0.35 | 0 | 0 | 0 | 0 | 0 | 0 | 0 | 0 |
| 389 | 0 | 0 | 0 | 0.6 | 0 | −1 | 0 | 0.4 | 0 | 0 | 0 | 0 | 0 | 0 | 0 | 0 |
| 390 | 0 | 0 | 0 | 0.55 | 0 | −1 | 0 | 0.45 | 0 | 0 | 0 | 0 | 0 | 0 | 0 | 0 |
| 391 | 0 | 0 | 0 | 0.5 | 0 | −1 | 0 | 0.5 | 0 | 0 | 0 | 0 | 0 | 0 | 0 | 0 |
| 392 | 0 | 0 | 0 | 0.45 | 0 | −1 | 0 | 0.55 | 0 | 0 | 0 | 0 | 0 | 0 | 0 | 0 |
| 393 | 0 | 0 | 0 | 0.4 | 0 | −1 | 0 | 0.6 | 0 | 0 | 0 | 0 | 0 | 0 | 0 | 0 |
| 394 | 0 | 0 | 0 | 0.35 | 0 | −1 | 0 | 0.65 | 0 | 0 | 0 | 0 | 0 | 0 | 0 | 0 |
| 395 | 0 | 0 | 0 | 0.3 | 0 | −1 | 0 | 0.7 | 0 | 0 | 0 | 0 | 0 | 0 | 0 | 0 |
| 396 | 0 | 0 | 0 | 0.25 | 0 | −1 | 0 | 0.75 | 0 | 0 | 0 | 0 | 0 | 0 | 0 | 0 |
| 397 | 0 | 0 | 0 | 0.2 | 0 | −1 | 0 | 0.8 | 0 | 0 | 0 | 0 | 0 | 0 | 0 | 0 |
| 398 | 0 | 0 | 0 | 0.15 | 0 | −1 | 0 | 0.85 | 0 | 0 | 0 | 0 | 0 | 0 | 0 | 0 |
| 399 | 0 | 0 | 0 | 0.1 | 0 | −1 | 0 | 0.9 | 0 | 0 | 0 | 0 | 0 | 0 | 0 | 0 |
| 400 | 0 | 0 | 0 | 0.05 | 0 | −1 | 0 | 0.95 | 0 | 0 | 0 | 0 | 0 | 0 | 0 | 0 |
| 401 | 0 | 0 | 0 | 0 | 0 | −1 | 0 | 1 | 0 | 0 | 0 | 0 | 0 | 0 | 0 | 0 |

APPENDIX A-continued

Simplified Steering Table

| Stim# | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 402 | 0.05 | 0 | 0 | 0 | 0 | −1 | 0 | 0.95 | 0 | 0 | 0 | 0 | 0 | 0 | 0 | 0 |
| 403 | 0.1 | 0 | 0 | 0 | 0 | −1 | 0 | 0.9 | 0 | 0 | 0 | 0 | 0 | 0 | 0 | 0 |
| 404 | 0.15 | 0 | 0 | 0 | 0 | −1 | 0 | 0.85 | 0 | 0 | 0 | 0 | 0 | 0 | 0 | 0 |
| 405 | 0.2 | 0 | 0 | 0 | 0 | −1 | 0 | 0.8 | 0 | 0 | 0 | 0 | 0 | 0 | 0 | 0 |
| 406 | 0.25 | 0 | 0 | 0 | 0 | −1 | 0 | 0.75 | 0 | 0 | 0 | 0 | 0 | 0 | 0 | 0 |
| 407 | 0.3 | 0 | 0 | 0 | 0 | −1 | 0 | 0.7 | 0 | 0 | 0 | 0 | 0 | 0 | 0 | 0 |
| 408 | 0.35 | 0 | 0 | 0 | 0 | −1 | 0 | 0.65 | 0 | 0 | 0 | 0 | 0 | 0 | 0 | 0 |
| 409 | 0.4 | 0 | 0 | 0 | 0 | −1 | 0 | 0.6 | 0 | 0 | 0 | 0 | 0 | 0 | 0 | 0 |
| 410 | 0.45 | 0 | 0 | 0 | 0 | −1 | 0 | 0.55 | 0 | 0 | 0 | 0 | 0 | 0 | 0 | 0 |
| 411 | 0.5 | 0 | 0 | 0 | 0 | −1 | 0 | 0.5 | 0 | 0 | 0 | 0 | 0 | 0 | 0 | 0 |
| 412 | 0.55 | 0 | 0 | 0 | 0 | −1 | 0 | 0.45 | 0 | 0 | 0 | 0 | 0 | 0 | 0 | 0 |
| 413 | 0.6 | 0 | 0 | 0 | 0 | −1 | 0 | 0.4 | 0 | 0 | 0 | 0 | 0 | 0 | 0 | 0 |
| 414 | 0.65 | 0 | 0 | 0 | 0 | −1 | 0 | 0.35 | 0 | 0 | 0 | 0 | 0 | 0 | 0 | 0 |
| 415 | 0.7 | 0 | 0 | 0 | 0 | −1 | 0 | 0.3 | 0 | 0 | 0 | 0 | 0 | 0 | 0 | 0 |
| 416 | 0.75 | 0 | 0 | 0 | 0 | −1 | 0 | 0.25 | 0 | 0 | 0 | 0 | 0 | 0 | 0 | 0 |
| 417 | 0.8 | 0 | 0 | 0 | 0 | −1 | 0 | 0.2 | 0 | 0 | 0 | 0 | 0 | 0 | 0 | 0 |
| 418 | 0.85 | 0 | 0 | 0 | 0 | −1 | 0 | 0.15 | 0 | 0 | 0 | 0 | 0 | 0 | 0 | 0 |
| 419 | 0.9 | 0 | 0 | 0 | 0 | −1 | 0 | 0.1 | 0 | 0 | 0 | 0 | 0 | 0 | 0 | 0 |
| 420 | 0.95 | 0 | 0 | 0 | 0 | −1 | 0 | 0.05 | 0 | 0 | 0 | 0 | 0 | 0 | 0 | 0 |
| 421 | 1 | 0 | 0 | 0 | 0 | −1 | 0 | 0 | 0 | 0 | 0 | 0 | 0 | 0 | 0 | 0 |
| 422 | 0.95 | 0 | 0 | 0.05 | 0 | −0.95 | −0.05 | 0 | 0 | 0 | 0 | 0 | 0 | 0 | 0 | 0 |
| 423 | 0.9 | 0 | 0 | 0.1 | 0 | −0.9 | −0.1 | 0 | 0 | 0 | 0 | 0 | 0 | 0 | 0 | 0 |
| 424 | 0.85 | 0 | 0 | 0.15 | 0 | −0.85 | −0.15 | 0 | 0 | 0 | 0 | 0 | 0 | 0 | 0 | 0 |
| 425 | 0.8 | 0 | 0 | 0.2 | 0 | −0.8 | −0.2 | 0 | 0 | 0 | 0 | 0 | 0 | 0 | 0 | 0 |
| 426 | 0.75 | 0 | 0 | 0.25 | 0 | −0.75 | −0.25 | 0 | 0 | 0 | 0 | 0 | 0 | 0 | 0 | 0 |
| 427 | 0.7 | 0 | 0 | 0.3 | 0 | −0.7 | −0.3 | 0 | 0 | 0 | 0 | 0 | 0 | 0 | 0 | 0 |
| 428 | 0.65 | 0 | 0 | 0.35 | 0 | −0.65 | −0.35 | 0 | 0 | 0 | 0 | 0 | 0 | 0 | 0 | 0 |
| 429 | 0.6 | 0 | 0 | 0.4 | 0 | −0.6 | −0.4 | 0 | 0 | 0 | 0 | 0 | 0 | 0 | 0 | 0 |
| 430 | 0.55 | 0 | 0 | 0.45 | 0 | −0.55 | −0.45 | 0 | 0 | 0 | 0 | 0 | 0 | 0 | 0 | 0 |
| 431 | 0.5 | 0 | 0 | 0.5 | 0 | −0.5 | −0.5 | 0 | 0 | 0 | 0 | 0 | 0 | 0 | 0 | 0 |
| 432 | 0.45 | 0 | 0 | 0.55 | 0 | −0.45 | −0.55 | 0 | 0 | 0 | 0 | 0 | 0 | 0 | 0 | 0 |
| 433 | 0.4 | 0 | 0 | 0.6 | 0 | −0.4 | −0.6 | 0 | 0 | 0 | 0 | 0 | 0 | 0 | 0 | 0 |
| 434 | 0.35 | 0 | 0 | 0.65 | 0 | −0.35 | −0.65 | 0 | 0 | 0 | 0 | 0 | 0 | 0 | 0 | 0 |
| 435 | 0.3 | 0 | 0 | 0.7 | 0 | −0.3 | −0.7 | 0 | 0 | 0 | 0 | 0 | 0 | 0 | 0 | 0 |
| 436 | 0.25 | 0 | 0 | 0.75 | 0 | −0.25 | −0.75 | 0 | 0 | 0 | 0 | 0 | 0 | 0 | 0 | 0 |
| 437 | 0.2 | 0 | 0 | 0.8 | 0 | −0.2 | −0.8 | 0 | 0 | 0 | 0 | 0 | 0 | 0 | 0 | 0 |
| 438 | 0.15 | 0 | 0 | 0.85 | 0 | −0.15 | −0.85 | 0 | 0 | 0 | 0 | 0 | 0 | 0 | 0 | 0 |
| 439 | 0.1 | 0 | 0 | 0.9 | 0 | −0.1 | −0.9 | 0 | 0 | 0 | 0 | 0 | 0 | 0 | 0 | 0 |
| 440 | 0.05 | 0 | 0 | 0.95 | 0 | −0.05 | −0.95 | 0 | 0 | 0 | 0 | 0 | 0 | 0 | 0 | 0 |
| 441 | 0 | 0 | 0 | 1 | 0 | 0 | −1 | 0 | 0 | 0 | 0 | 0 | 0 | 0 | 0 | 0 |
| 442 | 0 | 0 | 0 | 0.95 | 0.05 | 0 | −1 | 0 | 0 | 0 | 0 | 0 | 0 | 0 | 0 | 0 |
| 443 | 0 | 0 | 0 | 0.9 | 0.1 | 0 | −1 | 0 | 0 | 0 | 0 | 0 | 0 | 0 | 0 | 0 |
| 444 | 0 | 0 | 0 | 0.85 | 0.15 | 0 | −1 | 0 | 0 | 0 | 0 | 0 | 0 | 0 | 0 | 0 |
| 445 | 0 | 0 | 0 | 0.8 | 0.2 | 0 | −1 | 0 | 0 | 0 | 0 | 0 | 0 | 0 | 0 | 0 |
| 446 | 0 | 0 | 0 | 0.75 | 0.25 | 0 | −1 | 0 | 0 | 0 | 0 | 0 | 0 | 0 | 0 | 0 |
| 447 | 0 | 0 | 0 | 0.7 | 0.3 | 0 | −1 | 0 | 0 | 0 | 0 | 0 | 0 | 0 | 0 | 0 |
| 448 | 0 | 0 | 0 | 0.65 | 0.35 | 0 | −1 | 0 | 0 | 0 | 0 | 0 | 0 | 0 | 0 | 0 |
| 449 | 0 | 0 | 0 | 0.6 | 0.4 | 0 | −1 | 0 | 0 | 0 | 0 | 0 | 0 | 0 | 0 | 0 |
| 450 | 0 | 0 | 0 | 0.55 | 0.45 | 0 | −1 | 0 | 0 | 0 | 0 | 0 | 0 | 0 | 0 | 0 |
| 451 | 0 | 0 | 0 | 0.5 | 0.5 | 0 | −1 | 0 | 0 | 0 | 0 | 0 | 0 | 0 | 0 | 0 |
| 452 | 0 | 0 | 0 | 0.45 | 0.55 | 0 | −1 | 0 | 0 | 0 | 0 | 0 | 0 | 0 | 0 | 0 |
| 453 | 0 | 0 | 0 | 0.4 | 0.6 | 0 | −1 | 0 | 0 | 0 | 0 | 0 | 0 | 0 | 0 | 0 |
| 454 | 0 | 0 | 0 | 0.35 | 0.65 | 0 | −1 | 0 | 0 | 0 | 0 | 0 | 0 | 0 | 0 | 0 |
| 455 | 0 | 0 | 0 | 0.3 | 0.7 | 0 | −1 | 0 | 0 | 0 | 0 | 0 | 0 | 0 | 0 | 0 |
| 456 | 0 | 0 | 0 | 0.25 | 0.75 | 0 | −1 | 0 | 0 | 0 | 0 | 0 | 0 | 0 | 0 | 0 |
| 457 | 0 | 0 | 0 | 0.2 | 0.8 | 0 | −1 | 0 | 0 | 0 | 0 | 0 | 0 | 0 | 0 | 0 |
| 458 | 0 | 0 | 0 | 0.15 | 0.85 | 0 | −1 | 0 | 0 | 0 | 0 | 0 | 0 | 0 | 0 | 0 |
| 459 | 0 | 0 | 0 | 0.1 | 0.9 | 0 | −1 | 0 | 0 | 0 | 0 | 0 | 0 | 0 | 0 | 0 |
| 460 | 0 | 0 | 0 | 0.05 | 0.95 | 0 | −1 | 0 | 0 | 0 | 0 | 0 | 0 | 0 | 0 | 0 |
| 461 | 0 | 0 | 0 | 0 | 1 | 0 | −1 | 0 | 0 | 0 | 0 | 0 | 0 | 0 | 0 | 0 |
| 462 | 0.05 | 0 | 0 | 0 | 0.95 | 0 | −1 | 0 | 0 | 0 | 0 | 0 | 0 | 0 | 0 | 0 |
| 463 | 0.1 | 0 | 0 | 0 | 0.9 | 0 | −1 | 0 | 0 | 0 | 0 | 0 | 0 | 0 | 0 | 0 |
| 464 | 0.15 | 0 | 0 | 0 | 0.85 | 0 | −1 | 0 | 0 | 0 | 0 | 0 | 0 | 0 | 0 | 0 |
| 465 | 0.2 | 0 | 0 | 0 | 0.8 | 0 | −1 | 0 | 0 | 0 | 0 | 0 | 0 | 0 | 0 | 0 |
| 466 | 0.25 | 0 | 0 | 0 | 0.75 | 0 | −1 | 0 | 0 | 0 | 0 | 0 | 0 | 0 | 0 | 0 |
| 467 | 0.3 | 0 | 0 | 0 | 0.7 | 0 | −1 | 0 | 0 | 0 | 0 | 0 | 0 | 0 | 0 | 0 |
| 468 | 0.35 | 0 | 0 | 0 | 0.65 | 0 | −1 | 0 | 0 | 0 | 0 | 0 | 0 | 0 | 0 | 0 |
| 469 | 0.4 | 0 | 0 | 0 | 0.6 | 0 | −1 | 0 | 0 | 0 | 0 | 0 | 0 | 0 | 0 | 0 |
| 470 | 0.45 | 0 | 0 | 0 | 0.55 | 0 | −1 | 0 | 0 | 0 | 0 | 0 | 0 | 0 | 0 | 0 |
| 471 | 0.5 | 0 | 0 | 0 | 0.5 | 0 | −1 | 0 | 0 | 0 | 0 | 0 | 0 | 0 | 0 | 0 |
| 472 | 0.55 | 0 | 0 | 0 | 0.45 | 0 | −1 | 0 | 0 | 0 | 0 | 0 | 0 | 0 | 0 | 0 |
| 473 | 0.6 | 0 | 0 | 0 | 0.4 | 0 | −1 | 0 | 0 | 0 | 0 | 0 | 0 | 0 | 0 | 0 |
| 474 | 0.65 | 0 | 0 | 0 | 0.35 | 0 | −1 | 0 | 0 | 0 | 0 | 0 | 0 | 0 | 0 | 0 |
| 475 | 0.7 | 0 | 0 | 0 | 0.3 | 0 | −1 | 0 | 0 | 0 | 0 | 0 | 0 | 0 | 0 | 0 |

APPENDIX A-continued

Simplified Steering Table

| | | | | | | | Electrode# | | | | | | | | | |
|---|---|---|---|---|---|---|---|---|---|---|---|---|---|---|---|---|
| Stim# | 1 | 2 | 3 | 4 | 5 | 6 | 7 | 8 | 9 | 10 | 11 | 12 | 13 | 14 | 15 | 16 |
| 476 | 0.75 | 0 | 0 | 0 | 0.25 | 0 | −1 | 0 | 0 | 0 | 0 | 0 | 0 | 0 | 0 | 0 |
| 477 | 0.8 | 0 | 0 | 0 | 0.2 | 0 | −1 | 0 | 0 | 0 | 0 | 0 | 0 | 0 | 0 | 0 |
| 478 | 0.85 | 0 | 0 | 0 | 0.15 | 0 | −1 | 0 | 0 | 0 | 0 | 0 | 0 | 0 | 0 | 0 |
| 479 | 0.9 | 0 | 0 | 0 | 0.1 | 0 | −1 | 0 | 0 | 0 | 0 | 0 | 0 | 0 | 0 | 0 |
| 480 | 0.95 | 0 | 0 | 0 | 0.05 | 0 | −1 | 0 | 0 | 0 | 0 | 0 | 0 | 0 | 0 | 0 |
| 481 | 1 | 0 | 0 | 0 | 0 | 0 | −1 | 0 | 0 | 0 | 0 | 0 | 0 | 0 | 0 | 0 |
| 482 | 0.95 | 0 | 0 | 0 | 0.05 | 0 | −0.95 | −0.05 | 0 | 0 | 0 | 0 | 0 | 0 | 0 | 0 |
| 483 | 0.9 | 0 | 0 | 0 | 0.1 | 0 | −0.9 | −0.1 | 0 | 0 | 0 | 0 | 0 | 0 | 0 | 0 |
| 484 | 0.85 | 0 | 0 | 0 | 0.15 | 0 | −0.85 | −0.15 | 0 | 0 | 0 | 0 | 0 | 0 | 0 | 0 |
| 485 | 0.8 | 0 | 0 | 0 | 0.2 | 0 | −0.8 | −0.2 | 0 | 0 | 0 | 0 | 0 | 0 | 0 | 0 |
| 486 | 0.75 | 0 | 0 | 0 | 0.25 | 0 | −0.75 | −0.25 | 0 | 0 | 0 | 0 | 0 | 0 | 0 | 0 |
| 487 | 0.7 | 0 | 0 | 0 | 0.3 | 0 | −0.7 | −0.3 | 0 | 0 | 0 | 0 | 0 | 0 | 0 | 0 |
| 488 | 0.65 | 0 | 0 | 0 | 0.35 | 0 | −0.65 | −0.35 | 0 | 0 | 0 | 0 | 0 | 0 | 0 | 0 |
| 489 | 0.6 | 0 | 0 | 0 | 0.4 | 0 | −0.6 | −0.4 | 0 | 0 | 0 | 0 | 0 | 0 | 0 | 0 |
| 490 | 0.55 | 0 | 0 | 0 | 0.45 | 0 | −0.55 | −0.45 | 0 | 0 | 0 | 0 | 0 | 0 | 0 | 0 |
| 491 | 0.5 | 0 | 0 | 0 | 0.5 | 0 | −0.5 | −0.5 | 0 | 0 | 0 | 0 | 0 | 0 | 0 | 0 |
| 492 | 0.45 | 0 | 0 | 0 | 0.55 | 0 | −0.45 | −0.55 | 0 | 0 | 0 | 0 | 0 | 0 | 0 | 0 |
| 493 | 0.4 | 0 | 0 | 0 | 0.6 | 0 | −0.4 | −0.6 | 0 | 0 | 0 | 0 | 0 | 0 | 0 | 0 |
| 494 | 0.35 | 0 | 0 | 0 | 0.65 | 0 | −0.5 | −0.5 | 0 | 0 | 0 | 0 | 0 | 0 | 0 | 0 |
| 495 | 0.3 | 0 | 0 | 0 | 0.7 | 0 | −0.45 | −0.55 | 0 | 0 | 0 | 0 | 0 | 0 | 0 | 0 |
| 496 | 0.25 | 0 | 0 | 0 | 0.75 | 0 | −0.4 | −0.6 | 0 | 0 | 0 | 0 | 0 | 0 | 0 | 0 |
| 497 | 0.2 | 0 | 0 | 0 | 0.8 | 0 | −0.35 | −0.65 | 0 | 0 | 0 | 0 | 0 | 0 | 0 | 0 |
| 498 | 0.15 | 0 | 0 | 0 | 0.85 | 0 | −0.3 | −0.7 | 0 | 0 | 0 | 0 | 0 | 0 | 0 | 0 |
| 499 | 0.1 | 0 | 0 | 0 | 0.9 | 0 | −0.25 | −0.75 | 0 | 0 | 0 | 0 | 0 | 0 | 0 | 0 |
| 500 | 0.05 | 0 | 0 | 0 | 0.95 | 0 | −0.2 | −0.8 | 0 | 0 | 0 | 0 | 0 | 0 | 0 | 0 |
| 501 | 0 | 0 | 0 | 0 | 1 | 0 | −0.15 | −0.85 | 0 | 0 | 0 | 0 | 0 | 0 | 0 | 0 |
| 502 | 0 | 0 | 0 | 0 | 0.95 | 0.05 | −0.1 | −0.9 | 0 | 0 | 0 | 0 | 0 | 0 | 0 | 0 |
| 503 | 0 | 0 | 0 | 0 | 0.9 | 0.1 | −0.05 | −0.95 | 0 | 0 | 0 | 0 | 0 | 0 | 0 | 0 |
| 504 | 0 | 0 | 0 | 0 | 0.85 | 0.15 | 0 | −1 | 0 | 0 | 0 | 0 | 0 | 0 | 0 | 0 |
| 505 | 0 | 0 | 0 | 0 | 0.8 | 0.2 | 0 | −1 | 0 | 0 | 0 | 0 | 0 | 0 | 0 | 0 |
| 506 | 0 | 0 | 0 | 0 | 0.75 | 0.25 | 0 | −1 | 0 | 0 | 0 | 0 | 0 | 0 | 0 | 0 |
| 507 | 0 | 0 | 0 | 0 | 0.7 | 0.3 | 0 | −1 | 0 | 0 | 0 | 0 | 0 | 0 | 0 | 0 |
| 508 | 0 | 0 | 0 | 0 | 0.65 | 0.35 | 0 | −1 | 0 | 0 | 0 | 0 | 0 | 0 | 0 | 0 |
| 509 | 0 | 0 | 0 | 0 | 0.6 | 0.4 | 0 | −1 | 0 | 0 | 0 | 0 | 0 | 0 | 0 | 0 |
| 510 | 0 | 0 | 0 | 0 | 0.55 | 0.45 | 0 | −1 | 0 | 0 | 0 | 0 | 0 | 0 | 0 | 0 |
| 511 | 0 | 0 | 0 | 0 | 0.5 | 0.5 | 0 | −1 | 0 | 0 | 0 | 0 | 0 | 0 | 0 | 0 |
| 512 | 0 | 0 | 0 | 0 | 0.45 | 0.55 | 0 | −1 | 0 | 0 | 0 | 0 | 0 | 0 | 0 | 0 |
| 513 | 0 | 0 | 0 | 0 | 0.4 | 0.6 | 0 | −1 | 0 | 0 | 0 | 0 | 0 | 0 | 0 | 0 |
| 514 | 0 | 0 | 0 | 0 | 0.35 | 0.65 | 0 | −1 | 0 | 0 | 0 | 0 | 0 | 0 | 0 | 0 |
| 515 | 0 | 0 | 0 | 0 | 0.3 | 0.7 | 0 | −1 | 0 | 0 | 0 | 0 | 0 | 0 | 0 | 0 |
| 516 | 0 | 0 | 0 | 0 | 0.25 | 0.75 | 0 | −1 | 0 | 0 | 0 | 0 | 0 | 0 | 0 | 0 |
| 517 | 0 | 0 | 0 | 0 | 0.2 | 0.8 | 0 | −1 | 0 | 0 | 0 | 0 | 0 | 0 | 0 | 0 |
| 518 | 0 | 0 | 0 | 0 | 0.15 | 0.85 | 0 | −1 | 0 | 0 | 0 | 0 | 0 | 0 | 0 | 0 |
| 519 | 0 | 0 | 0 | 0 | 0.1 | 0.9 | 0 | −1 | 0 | 0 | 0 | 0 | 0 | 0 | 0 | 0 |
| 520 | 0 | 0 | 0 | 0 | 0.05 | 0.95 | 0 | −1 | 0 | 0 | 0 | 0 | 0 | 0 | 0 | 0 |
| 521 | 0 | 0 | 0 | 0 | 0 | 1 | 0 | −1 | 0 | 0 | 0 | 0 | 0 | 0 | 0 | 0 |
| 522 | 0 | 0.05 | 0 | 0 | 0 | 0.95 | 0 | −1 | 0 | 0 | 0 | 0 | 0 | 0 | 0 | 0 |
| 523 | 0 | 0.1 | 0 | 0 | 0 | 0.9 | 0 | −1 | 0 | 0 | 0 | 0 | 0 | 0 | 0 | 0 |
| 524 | 0.05 | 0.1 | 0 | 0 | 0 | 0.85 | 0 | −1 | 0 | 0 | 0 | 0 | 0 | 0 | 0 | 0 |
| 525 | 0.1 | 0.1 | 0 | 0 | 0 | 0.8 | 0 | −1 | 0 | 0 | 0 | 0 | 0 | 0 | 0 | 0 |
| 526 | 0.1 | 0.15 | 0 | 0 | 0 | 0.75 | 0 | −1 | 0 | 0 | 0 | 0 | 0 | 0 | 0 | 0 |
| 527 | 0.1 | 0.2 | 0 | 0 | 0 | 0.7 | 0 | −1 | 0 | 0 | 0 | 0 | 0 | 0 | 0 | 0 |
| 528 | 0.15 | 0.2 | 0 | 0 | 0 | 0.65 | 0 | −1 | 0 | 0 | 0 | 0 | 0 | 0 | 0 | 0 |
| 529 | 0.2 | 0.2 | 0 | 0 | 0 | 0.6 | 0 | −1 | 0 | 0 | 0 | 0 | 0 | 0 | 0 | 0 |
| 530 | 0.2 | 0.25 | 0 | 0 | 0 | 0.55 | 0 | −1 | 0 | 0 | 0 | 0 | 0 | 0 | 0 | 0 |
| 531 | 0.2 | 0.3 | 0 | 0 | 0 | 0.5 | 0 | −1 | 0 | 0 | 0 | 0 | 0 | 0 | 0 | 0 |
| 532 | 0.25 | 0.3 | 0 | 0 | 0 | 0.45 | 0 | −1 | 0 | 0 | 0 | 0 | 0 | 0 | 0 | 0 |
| 533 | 0.3 | 0.3 | 0 | 0 | 0 | 0.4 | 0 | −1 | 0 | 0 | 0 | 0 | 0 | 0 | 0 | 0 |
| 534 | 0.3 | 0.35 | 0 | 0 | 0 | 0.35 | 0 | −1 | 0 | 0 | 0 | 0 | 0 | 0 | 0 | 0 |
| 535 | 0.3 | 0.4 | 0 | 0 | 0 | 0.3 | 0 | −1 | 0 | 0 | 0 | 0 | 0 | 0 | 0 | 0 |
| 536 | 0.35 | 0.4 | 0 | 0 | 0 | 0.25 | 0 | −1 | 0 | 0 | 0 | 0 | 0 | 0 | 0 | 0 |
| 537 | 0.4 | 0.4 | 0 | 0 | 0 | 0.2 | 0 | −1 | 0 | 0 | 0 | 0 | 0 | 0 | 0 | 0 |
| 538 | 0.4 | 0.45 | 0 | 0 | 0 | 0.15 | 0 | −1 | 0 | 0 | 0 | 0 | 0 | 0 | 0 | 0 |
| 539 | 0.4 | 0.5 | 0 | 0 | 0 | 0.1 | 0 | −1 | 0 | 0 | 0 | 0 | 0 | 0 | 0 | 0 |
| 540 | 0.45 | 0.5 | 0 | 0 | 0 | 0.05 | 0 | −1 | 0 | 0 | 0 | 0 | 0 | 0 | 0 | 0 |
| 541 | 0.5 | 0.5 | 0 | 0 | 0 | 0 | 0 | −1 | 0 | 0 | 0 | 0 | 0 | 0 | 0 | 0 |

What is claimed is:

1. A system for an electrical neurostimulator coupled to a plurality of electrodes, comprising:
a processor configured for defining a target current source multipole relative to the plurality of electrodes, emulating the target multipole by defining an initial electrical current distribution for the electrodes, such that a first set of active electrodes respectively has electrical current values of a first polarity, and a second set of active electrodes respectively has electrical current values of a second polarity, comparing each of the electrical current values of the first polarity to a first threshold value, zeroing-out at least one of the electrodes in the first active electrode set based on the comparison, and redistributing the electrical current value of each of the at least one zeroed-out electrode in the first active electrode set to remaining ones of the electrodes in the first active electrode set to define a new electrical current distribution for the electrodes; and a controller configured for instructing the electrical neurostimulator to convey electrical current to the plurality of electrodes in accordance with the new electrical current distribution.

2. The system of claim 1, wherein the processor is further configured for comparing each of the electrical current values of the second polarity to a second threshold value, zeroing-out at least one of the electrodes in the second active electrode set based on the comparison, and redistributing the electrical current value of each of the at least one zeroed-out electrode in the second active electrode set to remaining ones of the electrodes in the second active electrode set to define the new electrical current distribution for the electrodes.

3. The system of claim 2, wherein the first threshold value and the second threshold value are equal to each other.

4. The system of claim 1, wherein the electrical values of the first polarity are fractionalized electrical current values.

5. The system of claim 1, wherein the first threshold value is an absolute threshold electrical current value, and the electrical current value of each of the at least one zeroed-out electrode in the first active electrode set is less than the absolute threshold electrical current value.

6. The system of claim 5, wherein the absolute threshold electrical current value is a fractionalized threshold electrical current value.

7. The system of claim 1, wherein the first threshold value is a function of a standard deviation less than the highest electrical current value of the first polarity, and the electrical current value of each of the at least one zeroed-out electrode in the first active electrode set is less than the first threshold value.

8. The system of claim 1, wherein the target multipole is one of a target bipole and a target tripole.

9. The system of claim 1, wherein the processor is configured for redistributing the electrical current value of each of the at least one zeroed-out electrode in the first active electrode set to the remaining electrodes in the first active electrode set in proportion to the electrical current values of the remaining electrodes in the first active electrode set.

10. The system of claim 1, further comprising telemetry circuitry, wherein the controller is further configured for instructing the electrical neurostimulator via the telemetry circuitry.

11. The system of claim 1, further comprising a housing containing the processor and controller.

12. A method of providing therapy to a patient using a plurality of electrodes implanted within the patient, comprising:

defining a target current source multipole relative to the plurality of electrodes;

emulating the target multipole by defining an initial electrical current distribution for the electrodes, such that a first set of active electrodes respectively has electrical current values of a first polarity, and a second set of active electrodes respectively has electrical current values of a second polarity;

comparing each of the electrical current values of the first polarity to a first threshold value;

zeroing-out at least one of the electrodes in the first active electrode set based on the comparison;

redistributing the electrical current value of each of the at least one zeroed-out electrode in the first active electrode set to remaining ones of the electrodes in the first active electrode set to define a new electrical current distribution for the electrodes; and conveying electrical current to the plurality of electrodes in accordance with the new electrical current distribution, thereby providing the therapy.

13. The method of claim 12, further comprising:

comparing each of the electrical current values of the second polarity to a second threshold value;

zeroing-out at least one of the electrodes in the second active electrode set based on the comparison; and redistributing the electrical current value of each of the at least one zeroed-out electrode in the second active electrode set to remaining ones of the electrodes in the second active electrode set to define the new electrical current distribution for the electrodes.

14. The method of claim 13, wherein the first threshold value and the second threshold value are equal to each other.

15. The method of claim 12, wherein the electrical values of the first polarity are fractionalized electrical current values.

16. The method of claim 12, wherein the first threshold value is an absolute threshold electrical current value, and the electrical current value of each of the at least one zeroed-out electrode in the first active electrode set is less than the absolute threshold electrical current value.

17. The method of claim 16, wherein the absolute threshold electrical current value is a fractionalized threshold electrical current value.

18. The method of claim 12, wherein the first threshold value is a function of a standard deviation less than the highest electrical current value of the first polarity, and the electrical current value of each of the at least one zeroed-out electrode in the first active electrode set is less than the first threshold value.

19. The method of claim 12, wherein the target multipole is one of a target bipole and a target tripole.

20. The method of claim 12, wherein the electrical current value of each of the at least one zeroed-out electrode in the first active electrode set is redistributed to the remaining electrodes in the first active electrode set in proportion to the electrical current values of the remaining electrodes in the first active electrode set.

* * * * *